(12) United States Patent
Holson et al.

(10) Patent No.: US 9,745,613 B2
(45) Date of Patent: Aug. 29, 2017

(54) COMPOUNDS, SUBSTRATES AND METHODS RELATED TO HISTONE DEACETYLASES

(71) Applicant: The Broad Institute, Inc., Cambridge, MA (US)

(72) Inventors: Edward Holson, Newton, MA (US); David Olson, Boston, MA (US)

(73) Assignee: The Broad Institute, Inc., Cambridge, MA (US)

( * ) Notice: Subject to any disclaimer, the term of this patent is extended or adjusted under 35 U.S.C. 154(b) by 48 days.

(21) Appl. No.: 14/805,867

(22) Filed: Jul. 22, 2015

(65) Prior Publication Data

US 2016/0060679 A1    Mar. 3, 2016

Related U.S. Application Data

(60) Provisional application No. 62/027,776, filed on Jul. 22, 2014.

(51) Int. Cl.

| | | |
|---|---|---|
| *C07D 209/04* | (2006.01) |
| *A61K 31/405* | (2006.01) |
| *C12Q 1/34* | (2006.01) |
| *A61K 31/185* | (2006.01) |
| *A61K 31/404* | (2006.01) |
| *A61K 31/4439* | (2006.01) |
| *A61K 31/397* | (2006.01) |
| *A61K 31/495* | (2006.01) |
| *A61K 31/4192* | (2006.01) |
| *A61K 31/365* | (2006.01) |
| *C07K 7/06* | (2006.01) |
| *C07D 209/08* | (2006.01) |
| *A61K 31/00* | (2006.01) |

(52) U.S. Cl.
CPC .............. *C12Q 1/34* (2013.01); *A61K 31/00* (2013.01); *A61K 31/185* (2013.01); *A61K 31/365* (2013.01); *A61K 31/397* (2013.01); *A61K 31/404* (2013.01); *A61K 31/4192* (2013.01); *A61K 31/4439* (2013.01); *A61K 31/495* (2013.01); *C07D 209/08* (2013.01); *C07K 7/06* (2013.01); *G01N 2333/98* (2013.01)

(58) Field of Classification Search
CPC .................................................. C07D 209/08
USPC .......................................... 548/469; 514/415
See application file for complete search history.

(56) References Cited

U.S. PATENT DOCUMENTS

| | | |
|---|---|---|
| 2004/0018579 A1 | 1/2004 | Cook |
| 2004/0091951 A1 | 5/2004 | Schultz et al. |
| 2007/0087400 A1 | 4/2007 | Darzins et al. |
| 2008/0293081 A1 | 11/2008 | Milne et al. |
| 2014/0335550 A1 | 11/2014 | Zhang et al. |

FOREIGN PATENT DOCUMENTS

| | | |
|---|---|---|
| GB | 2459976 A | 11/2009 |
| WO | 02/12267 A1 | 2/2002 |
| WO | 2010/092381 A1 | 8/2010 |
| WO | 2010/121023 A2 | 10/2010 |
| WO | 2011/019393 A2 | 2/2011 |

OTHER PUBLICATIONS

Hu, M., et al., "Supporting Information: Multi-Color, One-and Two-Photon Imaging of Enzymatic Activities in Live Cells with Fluorescently Quenched Activity-Based Probes (qABPs)," J. Am. Chem. Soc., 133(31): 12009-12020 (2011).
Jiskoot, W., et al., "Preparation and Application of a Fluorescein-Labeled Peptide for Determining the Affinity Constant of a Monoclonal Antibody-Hapten Complex by Fluorescence Polarization," Anal. Biochem., 196(2): 421-426 (1991).
Dumelin, C. E., et al., "A Portable Albumin Binder from a DNA-Encoded Chemical Library," Angew. Chem. Int. Ed., 47(17): 3196-3201 (2008).
Ikeda, M., et al., "Development of a DNA-binding TEMPO derivative for evaluation of nuclear oxidative stress and its application in living cells," Free Radical Biology and Medicine, 49(11): 1792-1797 (2010).
Wollack, J. W., et al., "Multifunctional Prenylated Peptides for live Cell Analysis," J. Am. Chem. Soc., 131(21): 7293-7303 (2009).
de Waart, D. R., et al., "Hepatic Transport Mechanisms of Cholyl-L-Lysyl-Fluorescein," J. Pharmacol. Exp. Therapeutics, 334(1): 78-86 (2010).
Mills, C. O., et al., "Different pathways of canalicular secretion of sulfated and non-sulfated fluorescent bile acids: a study in isolated hepatocyte couplets and TR-rats," J. Hepatology, 31(4): 678-684 (1999).
Lohse, J., et al., "Fluorescein-Conjugated Lysine Monomers for Solid Phase Synthesis of Fluorescent Peptides and PNA Oligomers," Bioconj. Chem., 8(4): 503-509 (1997).
Wegener, D,, et al., "A Fluorogenic Histone Deacetylase Assay Well Suited for High-Throughput Activity Screening" Chemistry & Biology, vol. 10, 61-68, Jan. 2003.

*Primary Examiner* — Raymond Henley, III
(74) *Attorney, Agent, or Firm* — Elmore Patent Law Group, P.C.; Mahreen Hoda; Carolyn Elmore

(57) ABSTRACT

The invention relates to methods for the identification of compounds, peptides and proteins that can act as substrates for histone deacetylases. The invention further relates to compounds of Formula I:

$$F_1\text{-}X_1\text{-}L_1\text{-}X_2\text{-}P_1\text{-}X_3\text{-}G_1 \qquad \text{(Formula I)}$$

The invention relates to the treatment of diseases or disorders mediated by ARID1A (BAF250A).

3 Claims, 14 Drawing Sheets

FIG. 7

COMPOUNDS, SUBSTRATES AND METHODS RELATED TO HISTONE DEACETYLASES

RELATED APPLICATION

This application claims the benefit of U.S. Provisional Application No. 62/027,776, filed on Jul. 22, 2014. The entire teachings of the above application are incorporated herein by reference.

GOVERNMENT SUPPORT

This invention was made with government support under Grant Nos. HG006093, GM040602, GM008597, CA160034, HHSN268201000033C, and HL096738 awarded by the National Institutes of Health, and DGE0718128 awarded by the National Science Foundation. The government has certain rights in the invention.

BACKGROUND OF THE INVENTION

Posttranslational acetylation of lysine residues is a highly conserved and important modification enabling the cellular calibration of protein function and/or stability resulting in effects ranging from cytoskeletal reorganization to changes in gene expression. (Weinert, B. T. et al. *Sci. Signal.* 4, ra48 (2011); Choudhary, C. et al. *Science* 325, 834-840 (2009); Spange, S., Wagner, T., Heinzel, T. & Krämer, O. H. *Int. J. Biochem. Cell Biol.* 41, 185-198 (2009); Fass, D. M. et al., "Histone Acetylation and Deacetylation," in *Epigenetic Regulation and Epigenomics*, ed. Meyers, R. A. (Wiley-Blackwell, Weinheim, 2012)). Histone deacetylases (HDACs) play a key role in maintaining the balance of acetylation states by catalyzing the removal of acetyl groups from the amino groups of acetylated lysine residues. (Fass, D. M. et al., "Histone Acetylation and Deacetylation," in *Epigenetic Regulation and Epigenomics*, ed. Meyers, R. A. (Wiley-Blackwell, Weinheim, 2012)). As a result, these enzymes have become important therapeutic targets for a number of disease states including, but not limited to, cancer and psychiatric illnesses. (Acharya, M. R., Sparreboom, A., Venitz, J. & Figg, W. D. *Mol. Pharmacol.* 68, 917-932 (2005); Griiff, J. & Tsai, L.-H. *Annu. Rev. Pharmacol. Toxicol.* 53, 311-330 (2013)). As their name implies, HDACs were thought to be primarily responsible for the deacetylation of histones; however, it has become apparent that a large number of non-histone proteins are substrates for these enzymes as well. (Choudhary, C. et al. *Science* 325, 834-840 (2009); Glozak, M. A., Sengupta, N., Zhang, X. & Seto, E. *Gene* 363, 15-23 (2005)). The HDAC family is comprised of the NAD(+)-dependent sirtuins (class III) and the metal-dependent HDACs, which can be further divided into three classes (class I: HDACs 1, 2, 3, and 8, class II: HDACs 4, 5, 6, 7, 9, 10, and class IV: HDAC11) based on phylogenetic similarity with class I being localized primarily in the nucleus and classes II and IV shuttling between the nucleus and the cytoplasm. (Gregoretti, I. V., Lee, Y.-M. & Goodson, H. V. *J. Mol. Biol.* 338, 17-31 (2004); Fass, D. M. et al., "Histone Acetylation and Deacetylation," in *Epigenetic Regulation and Epigenomics*, ed. Meyers, R. A. (Wiley-Blackwell, Weinheim, 2012)).

Identification of the endogenous substrates of HDAC enzymes is a fundamental area of HDAC research, and this problem has been particularly acute for the class I enzyme HDAC8. Of all the HDACs, HDAC8 is arguably the best characterized structurally. (Buggy, J. J., Sideris, M. L., Mak, P., Lorimer, D. D., McIntosh, B., Clark, J. M. (2000) Cloning and characterization of a novel human histone deacetylase, HDAC8. *Biochem. J.* 350, 199-205; Estiu, G., West, N., Mazitschek, R., Greenberg, E., Bradner, J. E., Wiest, O. (2010) On the inhibition of histone deacetylase 8. *Bioorg. Med. Chem.* 18, 4103-4110; Tang et al., *Bioorganic & Medicinal Chemistry Letters* 21 (2011) 2601-2605; Galletti et al., *ChemMedChem* 2009, 4, 1991-2001; KrennHrubec et al., *Bioorganic & Medicinal Chemistry Letters* 17 (2007) 2874-2878; Suzuki T., et al., *J. Med. Chem.* 2012, 55, 9562-9575; Bieliauskas A V et al., *Chem Soc Rev.* 2008 37(7), 1402-1413). It was the first human class I HDAC structure to be reported, and since then, over 25 additional structures bound to various classes of small molecule ligands and peptides have been disclosed (www.p-db.org). (Wolfson, N. A., Pitcairn, C. A., Fierke, C. A. (2012) HDAC8 substrates: Histones and beyond. *Biopolymers* 99, 112-126). However, despite this knowledge, few of the enzyme's natural substrates have been identified. (Wolfson et al.) To date, only two cellular substrates of HDAC8 have been identified, namely, the estrogen-related receptor alpha (ERR-α) and the structural maintenance of chromosome 3 (SMC3) protein, of which the latter plays a prominent role in Cornelia de Lange syndrome. (Wilson, B. J., Tremblay, A. M., Deblois, G., Sylvain-Drolet, G., Giguère, V. (2010) An acetylation switch modulates the transcriptional activity of estrogen-related receptor alpha *Mol. Endocrinol.* 24, 1349-1358; Deardorff, M. A. et al., (2012) HDAC8 mutations in Cornelia de Lange syndrome affect the cohesin acetylation cycle. *Nature* 489, 313-317).

It remains unclear which, if any, specific histone residues serve as viable substrates for this isoform. In terms of biological function, HDAC8 has been implicated in various cancers including neuroblastoma, urothelial, and breast cancer as well as in neural crest development. (Oehme, I. et al., (2009) Histone deacetylase 8 in neuroblastoma tumorigenesis. *Clin. Cancer Res.* 15, 91-99; Niegisch, G. et al., (2013) Changes in histone deacetylase (HDAC) expression patterns and activity of HDAC inhibitors in urothelial cancers. *Urol. Oncol-Semin. Ori.* 31, 1770-1779; Park, S. Y. et al., (2011) Histone deacetylases 1, 6 and 8 are critical for invasion in breast cancer. *Oncol. Rep.* 25, 1677-1681; Haberland, M., Mokalled, M. H., Montgomery, R. L., Olson, E. N. (2009) Epigenetic control of skull morphogenesis by histone deacetylase 8. *Genes Dev.* 23, 1625-1630). The HDAC8 substrates that mediate these effects are currently unknown.

SUMMARY OF THE INVENTION

The invention relates to methods for identifying substrates including proteins and peptides modified by histone deacetylases and in particular, HDAC8. The invention further relates to identifying inhibitors of activity mediated by said substrates of histone deacetylases and the use of said inhibitors in the treatment of diseases or disorders mediated by said substrates.

The invention further relates to the methods for identifying agents that can selectively inhibit specific isoforms of histone deacetylases, including HDAC8. In one embodiment, the invention relates to identifying non-histone substrates of histone deacetylases and in particular identification of non-histone nuclear substrates of histone deacetylases that are selectively deacetylated by one or more isoforms of HDAC, in particular HDAC8.

The invention further relates to the treatment of diseases or disorders mediated by substrates of histone deacetylases, in particular ARID1A. In particular, the invention relates to the treatment of cell proliferative disorders including cancer, such as, gynecologic cancer (including ovarian cancer and ovarian clear-cell carcinoma), gastric cancer, hepatocellular carcinoma, breast cancer, uterine endometrioid carcinoma, uterine clear-cell carcinoma, pancreatic cancer, transitional-cell carcinoma or bladder, Waldenstrom macrogloblinemia, anaplastic thyroid cancer, renal cancer, colon cancer, lung cancer, cervical adenocarcinoma, bile duct cancer, prostate cancer and medulloblastoma.

The invention further relates to a method for the treatment of a disease or condition mediated by a protein selected from CENPF, NCOA3, SMC3, RAI1, ZRANB2, SRSF5, CSRP2BP, MAML1, PPIL2, THRAP3 and MLL2 comprising the step of administering an inhibitor of HDAC8 to a subject in need thereof.

In a preferred embodiment, a selective HDAC8 inhibitor is selected from:

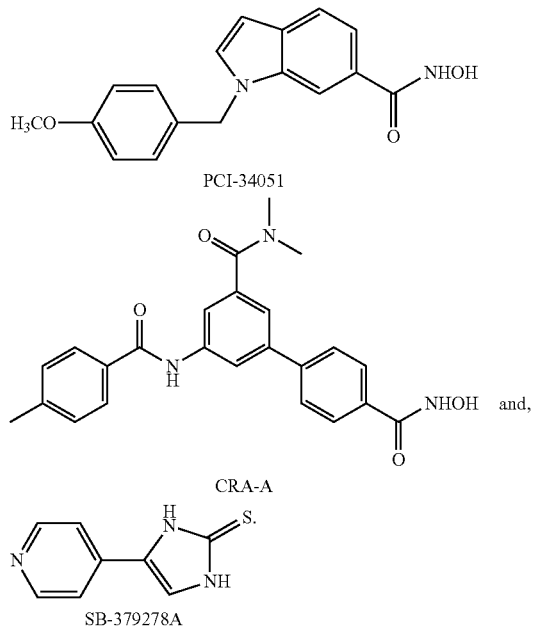

The invention further relates to a method for the treatment of a disease or condition mediated by the aberrant expression of a gene selected from HMOX1, IGF1R, CRK, CDKN1B, CDK1, CDKN1A (p21), CDK4 and TP53 comprising the step of administering an inhibitor of HDAC8, preferably, a selective inhibitor of HDAC8 to a subject in need thereof. The invention further relates to a method for the treatment of a disease or condition mediated by the expression of a gene product encoded by a gene selected from HMOX1, IGF1R, CRK, CDKN1B, CDK1, CDKN1A (p21), CDK4 and TP53 comprising the step of administering an inhibitor of HDAC8, preferably, a selective inhibitor of HDAC8 to a subject in need thereof.

The invention further relates to fluorescent compounds that are conjugates to HDAC substrates and methods of using the conjugates for identifying agents that can selectively affect the activity of one or more HDAC isoforms. For example, the invention relates to compounds of Formula I:

$F_1$-$X_1$-$L_1$-$X_2$-$P_1$-$X_3$-$G_1$         (Formula I).

The invention further relates to a method for determining lysine deacetylase activity of a protein or peptide comprising the step of incubating said protein or peptide with a compound according to Formula I and monitoring the modification of a lysine residue of said compound of Formula I over time.

The invention further relates to a method for assessing acetylation or deacetylation activity in a cell line, comprising the steps of: (i) providing a first and second cell lines having histone deacetylase or one or more Sirtuin activity; (ii) contacting said first cell line with an inhibitor of one or more isoforms of HDAC or Sirtuin; (iii) wherein said second line is not contacted with an inhibitor of HDAC or Sirtuin; (iv) incubating said first and second cell lines with one or more isoforms of HDAC or Sirtuin; and assessing the level of acetylation in said first and second cell lines: and comparing the levels of acetylation of first cell line with the acetylation of a second cell line.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

(b) LCMS trace depicting the elution of BRD3811 at Rt=1.14 min. DMSO elutes at Rt=0.10.

Figure 9:
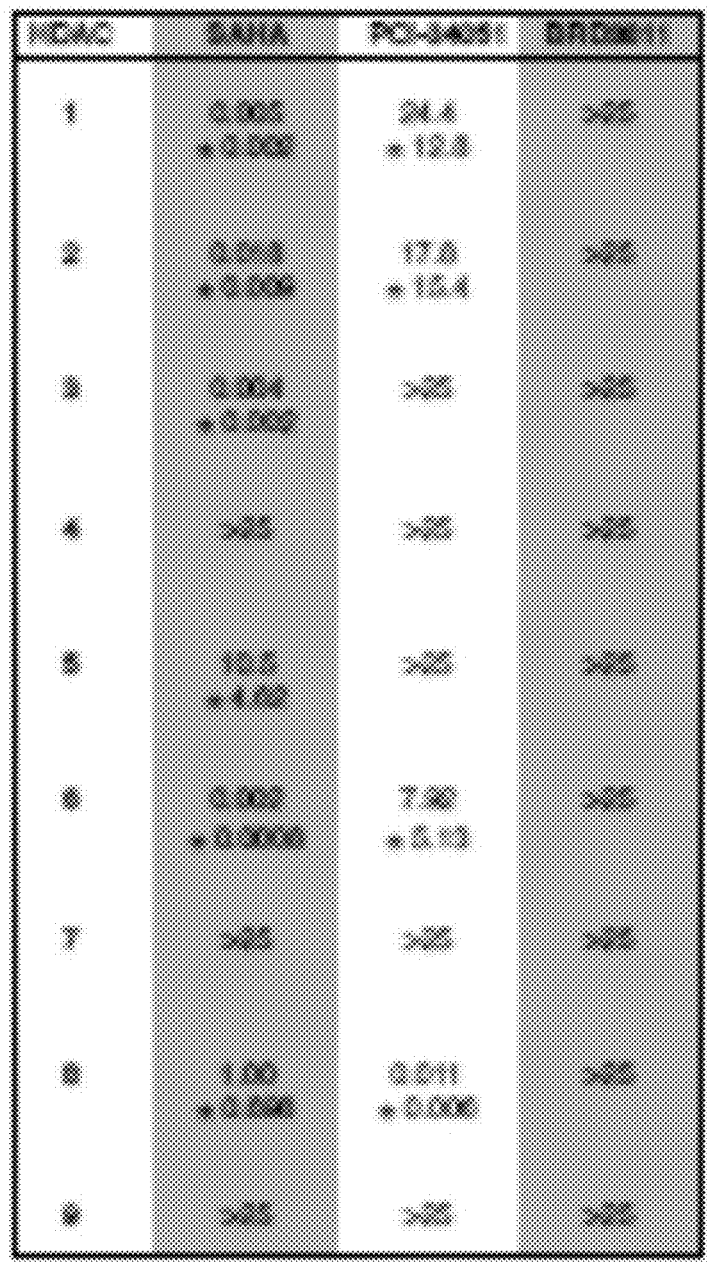

FIG. 9: IC50 values for compounds used in this study. IC50 values were determined using the caliper assay (see methods for details) and are reported as mean of at least four experiments±standard deviation.

Figure 10:
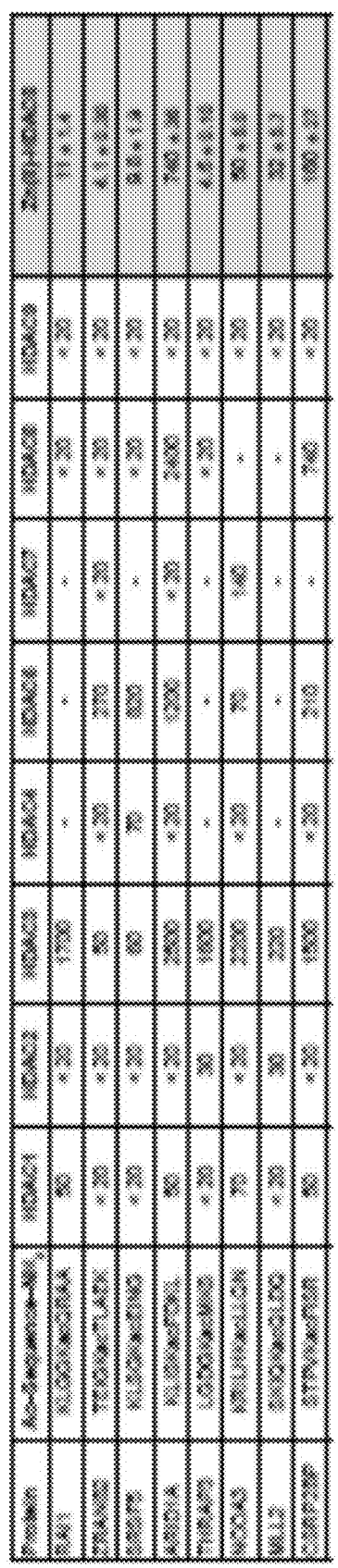

FIG. 10: In vitro peptide deacetylation catalyzed by commercially available HDACs. The initial rate for acetate production, determined from 1-2 time points, was measured using commercially available recombinant HDAC 1-9 (0.4 µM, purchased from BPS Biosciences) and acetylated peptide (100 µM) in assay buffer (2.7 mM KCl, 137 mM NaCl, 50 mM HEPES, pH 7.8). The value of kcat/KM (in M−1s−1) was calculated assuming a linear dependence on the substrate concentration. Dashes indicate particular combinations of peptides and enzyme isoforms that were not measured. The HDAC8 purified from baculovirus has higher specific activity than the recombinant enzyme purified from *E. coli*. Values (±standard error) obtained using HDAC8 purified from baculovirus are listed in grey for comparison.

DETAILED DESCRIPTION OF THE INVENTION

The invention relates to methods for identifying substrates including proteins and peptides modified by histone deacetylases and in particular, HDAC8. The invention further relates to identifying inhibitors of activity mediated by said substrates of histone deacetylases and the use of said inhibitors in the treatment of diseases or disorders mediated by said substrates.

The invention further relates to the methods for identifying agents that can selectively inhibit specific isoforms of histone deacetylases, including HDAC8. In one embodiment, the invention relates to identifying non-histone substrates of histone deacetylases and in particular identification of non-histone nuclear substrates of histone deacetylases that are selectively deacetylated by one or more isoforms of HDAC.

The invention further relates to the treatment of diseases or disorders mediated by substrates of histone deacetylases, in particular ARID1A. In particular, the invention relates to the treatment of cell proliferative disorders including cancer, such as, gynecologic cancer, including ovarian cancer.

The invention further relates to a method for the treatment of a disease or condition mediated by a protein selected from CENPF, NCOA3, SMC3, RAI1, ZRANB2, SRSF5, CSRP2BP, MAML1, PPIL2, THRAP3 or MLL2 comprising the step of administering an inhibitor of HDAC8 to a subject in need thereof.

In a preferred embodiment, a selective HDAC8 inhibitor is selected from:

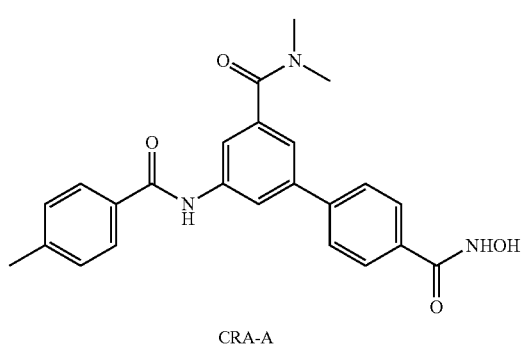

CRA-A

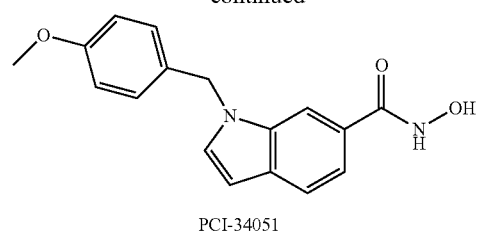
PCI-34051
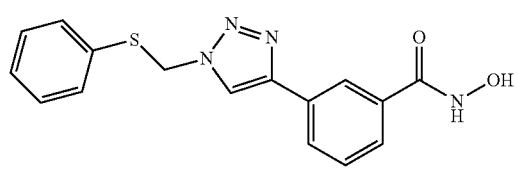
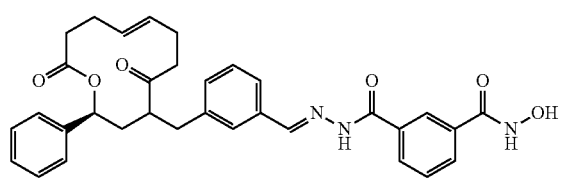
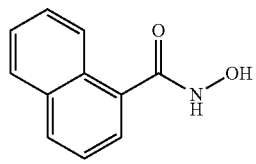
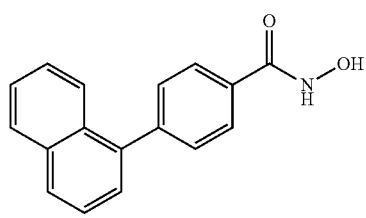
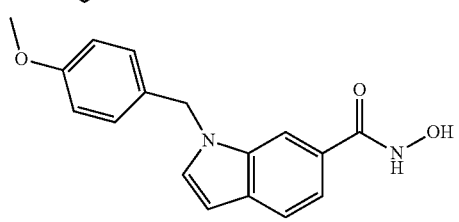
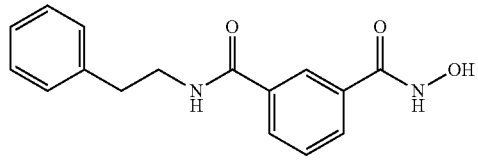
BRD73954
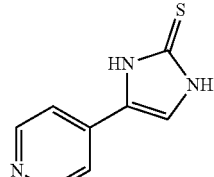
SB-379278A
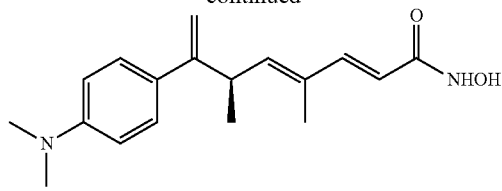
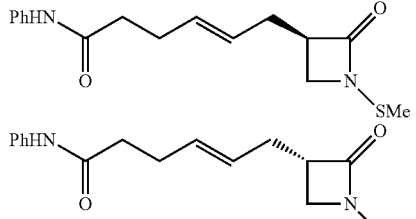
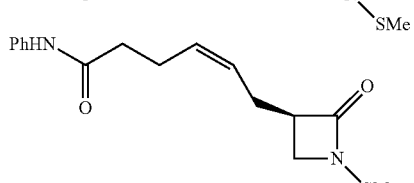
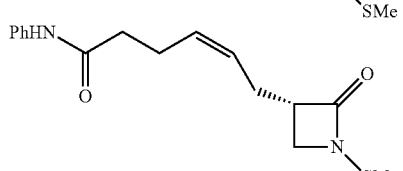
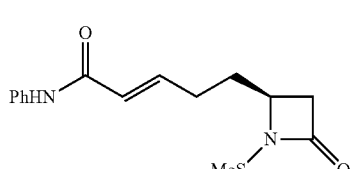
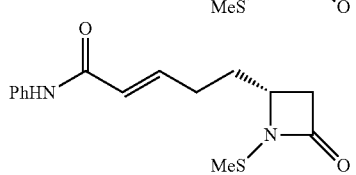
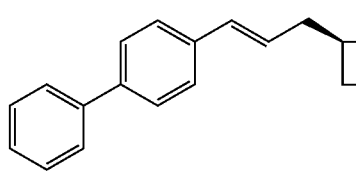
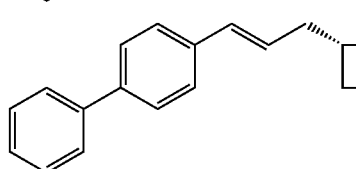
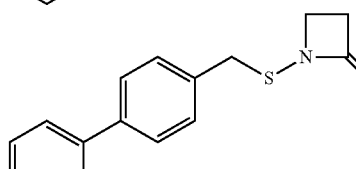
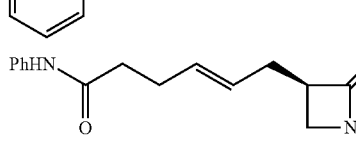

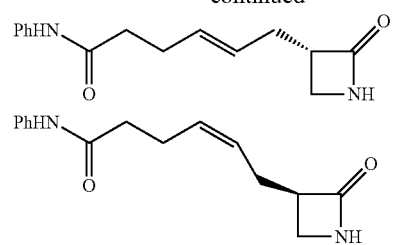
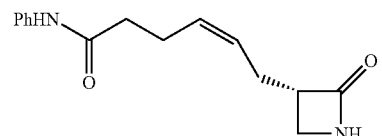
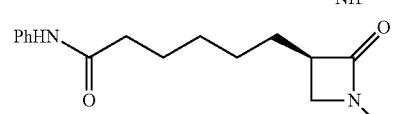
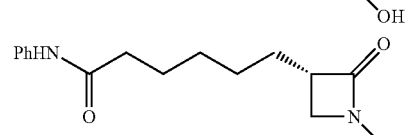
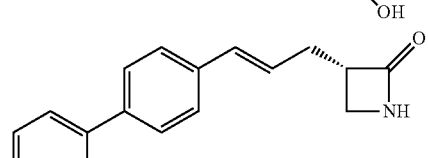
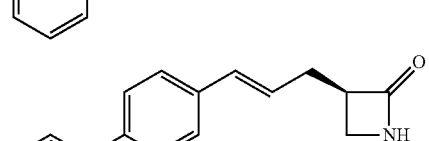
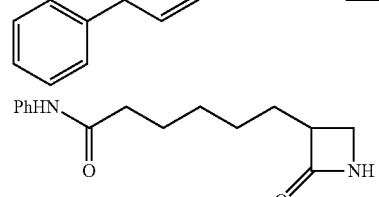
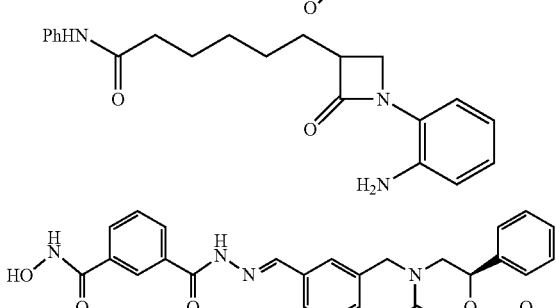
A8B4
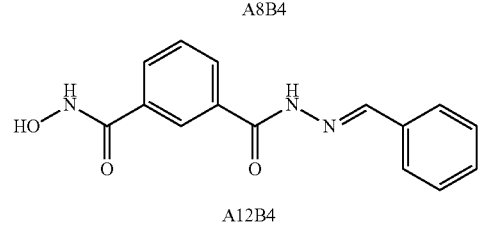
A12B4
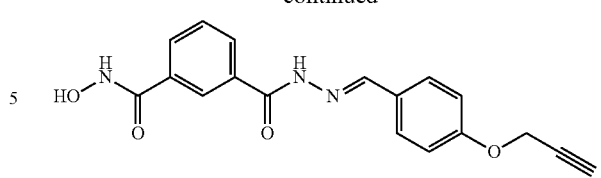
A14B4
1
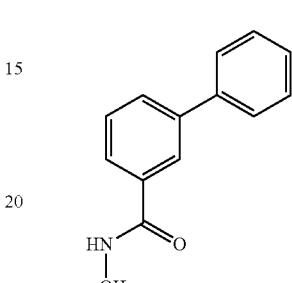
2
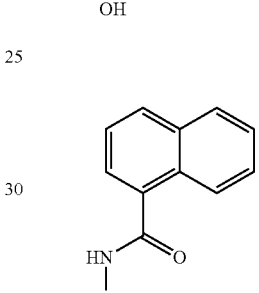
3
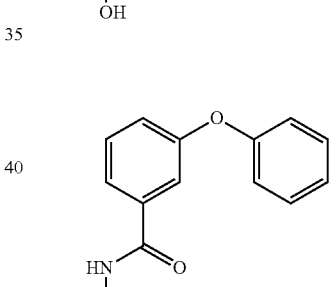
4
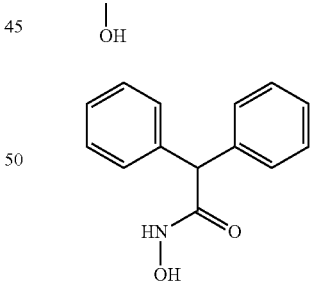
5
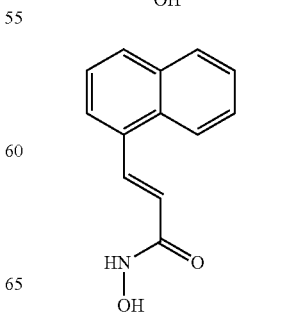

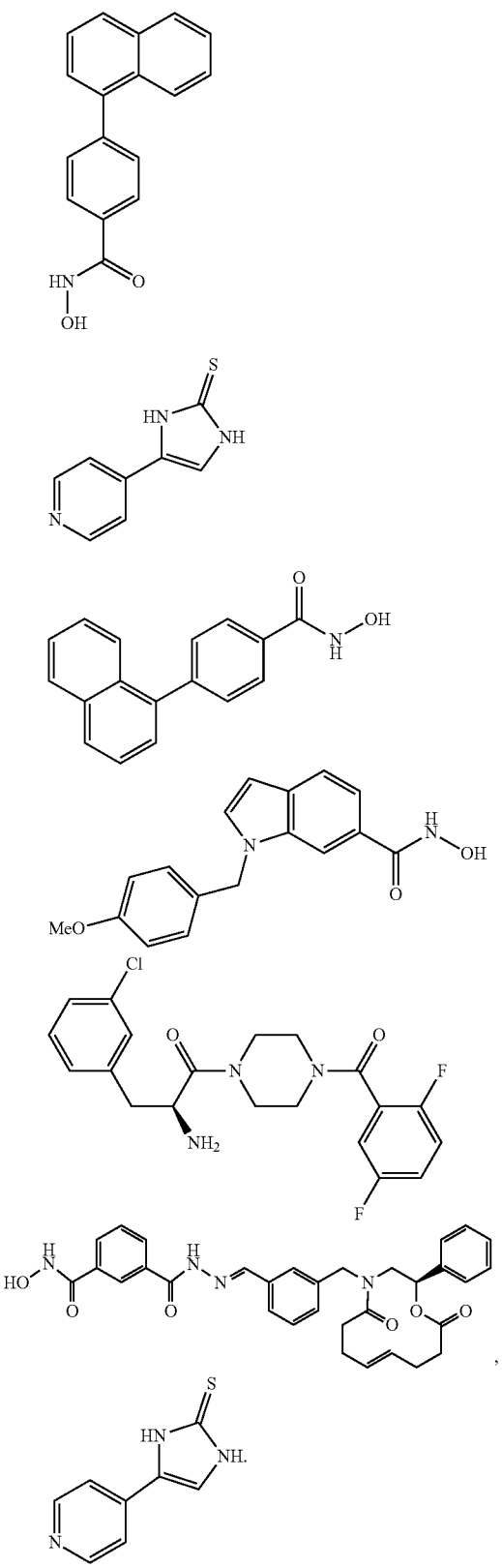

The invention further relates to a method for the treatment of a disease or condition mediated by the aberrant expression of a gene selected from HMOX1, IGF1R, CRK, CDKN1B, CDK1, CDKN1A (p21), CDK4 and TP53 comprising the step of administering an inhibitor of HDAC8, preferably, a selective inhibitor of HDAC8 to a subject in need thereof. The invention further relates to a method for the treatment of a disease or condition mediated by the expression of a gene product encoded by a gene selected from HMOX1, IGF1R, CRK, CDKN1B, CDK1, CDKN1A (p21), CDK4 and TP53 comprising the step of administering an inhibitor of HDAC8, preferably, a selective inhibitor of HDAC8 to a subject in need thereof.

The invention further relates to fluorescent compounds that are conjugates to HDAC substrates and methods of using the conjugates for identifying agents that can selectively affect the activity of one or more HDAC isoforms. For example, the invention relates to compounds of Formula I:

$F_1$-$X_1$-$L_1$-$X_2$-$P_1$-$X_3$-$G_1$ (Formula I)

wherein $F_1$ is a fluorophore; preferably a fluorescein-based fluorophore; more preferably, 6-carboxy fluorescein (FAM);

$L_1$ is alkyl, substituted alkyl, alkenyl, substituted alkenyl, alkynyl, substituted alkynyl, —O—, —S—, —[C($R_{10}$)($R_{11}$)]$_t$—, —N($R_{10}$)—, —N($R_{10}$)[C($R_{10}$)($R_{11}$)]$_t$, —O[C($R_{10}$)($R_{11}$)]$_t$—, —O[C($R_{10}$)($R_{11}$)C($R_{10}$)($R_{11}$)O]$_u$— or —S[C($R_{10}$)($R_{11}$)]$_t$-aliphatic or substituted aliphatic;

wherein t is 0, 1, 2, 3, 4, 5, 6, 7, 8, 9, 10, 11, 12, 13, 14, 15, 16, 17, 18, 19, 20, 21, 22, 23 or 24;

u is an integer between 1 and 500;

wherein $R_{10}$ and $R_{11}$ is independently hydrogen, halogen, —O$R_{20}$, —S$R_{20}$, —N$R_{20}R^{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$ and $R_{11}$ groups together with the atoms to which they are attached and any intervening atoms may form an additional optionally substituted, 3, 4, 5, 6 or 7 membered ring;

wherein each $R_{20}$ and $R_{21}$ is independently hydrogen, aliphatic, substituted aliphatic, aromatic or substituted aromatic;

$P_1$ is a peptide or protein that can act as a substrate for a sirtuin protein (SIRT) or a substrate that is selective for an isoform of HDAC or a non-histone substrate of any one or more of HDAC isoforms or a pan-HDAC non-histone substrate; preferably, $P_1$ is a selective substrate for HDAC8; Preferably $P_1$ is a non-histone substrate of HDAC; preferably, $P_1$ is a peptide or protein comprising the amino acid sequence of SEQ ID NO: 1-34:

KLGGK(Ac)QRAA; (SEQ ID NO: 1)

TEIGK(Ac)TLAEK; (SEQ ID NO: 2)

LGDGK(Ac)MKS; (SEQ ID NO: 3)

KRILHK(Ac)LLQN; (SEQ ID NO: 4)

KLSGK(Ac)EING; (SEQ ID NO: 5)

KLISK(Ac)FDKL;                     (SEQ ID NO: 6)

STPVK(Ac)FISR;                     (SEQ ID NO: 7)

SKIQK(Ac)QLDQ;                     (SEQ ID NO: 8)

RVIGAKK(Ac)DQY;                    (SEQ ID NO: 9)

KLGGK(COCF$_3$)QRAA;               (SEQ ID NO: 10)

TEIGK(COCF$_3$)TLAEK;              (SEQ ID NO: 11)

LGDGK(COCF$_3$)MKS;                (SEQ ID NO: 12)

KRILHK(COCF$_3$)LLQN;              (SEQ ID NO: 13)

KLSGK(COCF$_3$)EING;               (SEQ ID NO: 14)

KLISK(COCF$_3$)FDKL;               (SEQ ID NO: 15)

STPVK(COCF$_3$)FISR;               (SEQ ID NO: 16)

SKIQK(COCF$_3$)QLDQ;               (SEQ ID NO: 17)

RVIGAKK(COCF$_3$)DQY;              (SEQ ID NO: 18)

K(Ac)FDKL;                         (SEQ ID NO: 19)

SK(Ac)FDKL;                        (SEQ ID NO: 20)

ISK(Ac)FDKL;                       (SEQ ID NO: 21)

LISK(Ac)FDKL;                      (SEQ ID NO: 22)

KLISK(Ac);                         (SEQ ID NO: 23)

KLISK(Ac)F;                        (SEQ ID NO: 24)

KLISK(Ac)FD;                       (SEQ ID NO: 25)

KLISK(Ac)FDK;                      (SEQ ID NO: 26)

K(COCF$_3$)FDKL;                   (SEQ ID NO: 27)

SK(COCF$_3$FDKL;                   (SEQ ID NO: 28)

ISK(COCF$_3$)FDKL;                 (SEQ ID NO: 29)

LISK(COCF$_3$)FDKL;                (SEQ ID NO: 30)

KLISK(COCF$_3$);                   (SEQ ID NO: 31)

KLISK(COCF$_3$)F;                  (SEQ ID NO: 32)

KLISK(COCF$_3$)FD;                 (SEQ ID NO: 33)

KLISK(COCF$_3$)FDK.                (SEQ ID NO: 34)

Preferably, $P_1$ is a peptide or protein comprising a fragment of amino acid sequence of SEQ ID NO: 1-34 comprising a modified lysine residue.

An example of a peptide that can be used according to the present invention is a peptide comprising the amino acid sequence of SEQ ID NO: 1-34, wherein the peptide is less than about 50 amino acids in length. In some embodiments, the peptide is less than about 45, 40, 35, 30, 25, 20, or 15 amino acids in length. In another embodiment, the peptide is a peptide consisting of an amino acid sequence having SEQ ID NO: 1-34. In yet another embodiment, the peptide comprises an amino acid sequence having at least about 80%, 85%, 90%, 95%, or 98% sequence identity to the amino acid sequence of SEQ ID NO: 1-34, wherein the peptide is less than about 50 amino acids in length. In a further embodiment, the peptide consists of an amino acid sequence having at least about 50%, 60%, 70%, 80%, 85%, 90%, 95%, or 98% sequence identity to the amino acid sequence of SEQ ID NO: 1-34. In some embodiments, the peptide is less than about 45, 40, 35, 30, 25, 20, or 15 amino acids in length.

Preferably, $P_1$ is a peptide having a sequence consisting of the following amino acid sequences: KLGGK(Ac)QRAA, TEIGK(Ac)TLAEK, LGDGK(Ac)MKS, KRILHK(Ac)LLQN, KLSGK(Ac)EING, KLISK(Ac)FDKL, STPVK(Ac)FISR, SKIQK(Ac)QLDQ, RVIGAKK(Ac)DQY, KLGGK(COCF$_3$)QRAA, TEIGK(COCF$_3$)TLAEK, LGDGK(COCF$_3$)MKS, KRILHK(COCF$_3$)LLQN, KLSGK(COCF$_3$)EING, KLISK(COCF$_3$)FDKL, STPVK(COCF$_3$)FISR, SKIQK(COCF$_3$)QLDQ, RVIGAKK(COCF$_3$)DQY. Preferably $P_1$ is a peptide or protein that has a modified lysine residue, for example acetylated or trifluoro acetylated lysine residue, that can act as a substrate for HDAC, preferably HDAC8, HDAC 3 or HDAC6 or SIRT wherein HDAC8 or SIRT can deacetylate the acetyl or trifluoro acetyl group. In one embodiment, the substrate has selectivity for HDAC6 and HDAC8 wherein selectivity over other HDAC isoforms is at least two times, three times, five times or ten times higher.

$G_1$ is H, —CONH$_2$, —COOH, —COOR$_{10}$, —C(O)R$_{10}$, —C(S)OR$_{10}$, —R$_{10}$ or a hydrophobic group; preferably, $G_1$ is an optionally substituted alkyl, optionally substituted alkenyl, optionally substituted alkynyl, optionally substituted aryl, optionally substituted heteroaryl group, an alkyl group substituted with an optionally substituted aryl or heteroaryl group, an alkenyl group substituted with an optionally substituted aryl or heteroaryl group or a natural or unnatural amino acid;

wherein each $X_1$, $X_2$, and $X_3$ is independently a direct bond, —O—, —S—, —C(O)—, —C(O)—NR$_{100}$—, —C(S)—, —C(S)—NR$_{100}$—, —C(O)O—, —NR$_{100}$— and —S(O)$_2$—; wherein R$_{100}$ is hydrogen, alkyl, substituted alkyl, aryl or substituted aryl.

In a preferred embodiment, $F_1$ is 6-carboxy fluorescein (6-FAM) or 5-carboxy fluorescein (5-FAM) or fluorescein isothiocyanate (FITC).

In a preferred embodiment, $L_1$ is an alkyl or $C_1$-$C_{10}$alkyl group.

In a preferred embodiment, $G_1$ is, methyl coumarin or coumarin or N-methyl-3-phenylpropanamide.

In a preferred embodiment, $X_1$ is selected from —O—, —C(O)NH—, —C(O)— and —C(O)O—.

In a preferred embodiment, $X_2$ is selected from —O—, —C(O)NH—, —C(O)— and —C(O)O—.

In a preferred embodiment, $X_3$ is selected from —O—, —C(O)NH—, —C(O)— and —C(O)O—.

In a preferred embodiment, $F_1$ is selected from Table A:

TABLE A

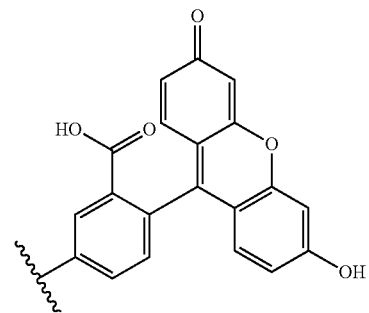 [SMILES: *c1ccc(-c2c3ccc(=O)cc-3oc3cc(O)ccc23)c(C(=O)O)c1]

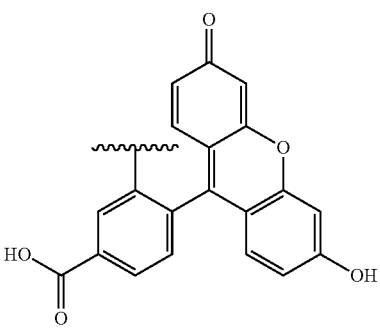 [SMILES: *c1cc(C(=O)O)ccc1-c1c2ccc(=O)cc-2oc2cc(O)ccc12]

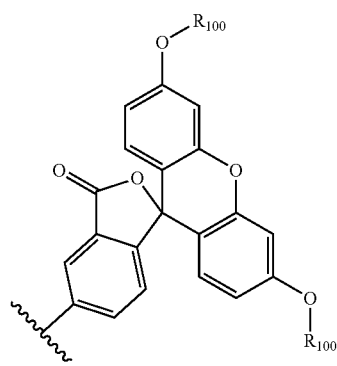

TABLE A-continued

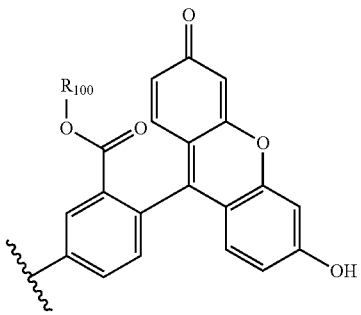

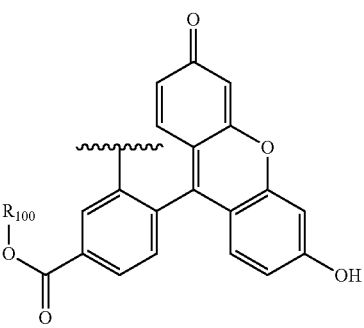

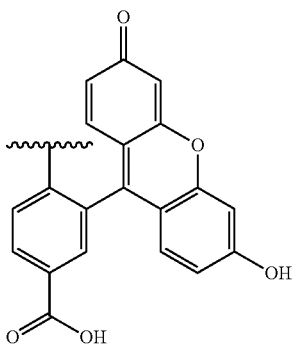

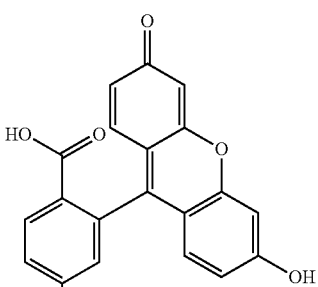

wherein $R_{100}$ is hydrogen, alkyl, substituted alkyl, aryl or substituted aryl.

In a preferred embodiment, $L_1$ is selected from Table B:

TABLE B

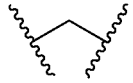

TABLE B-continued

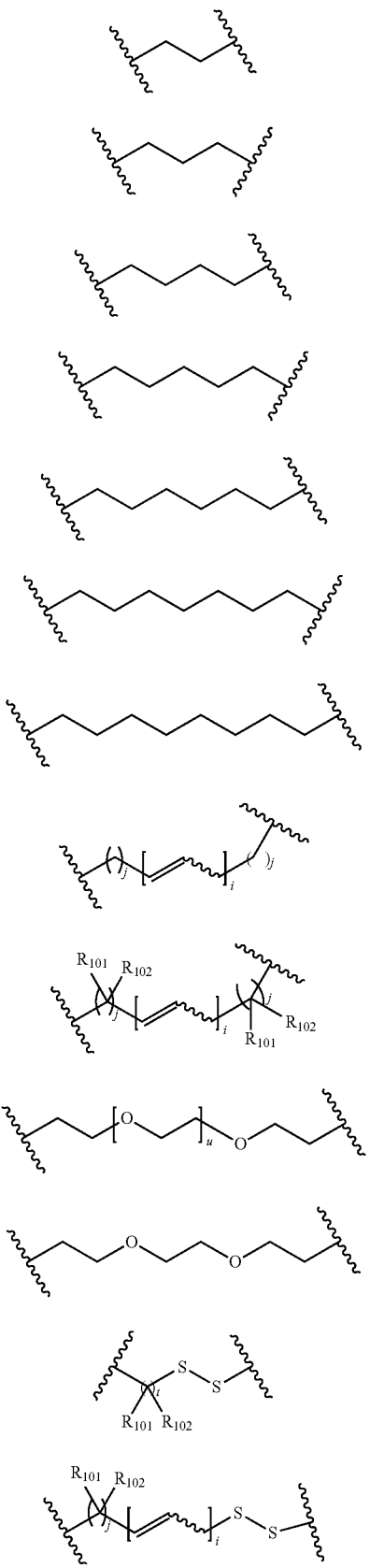

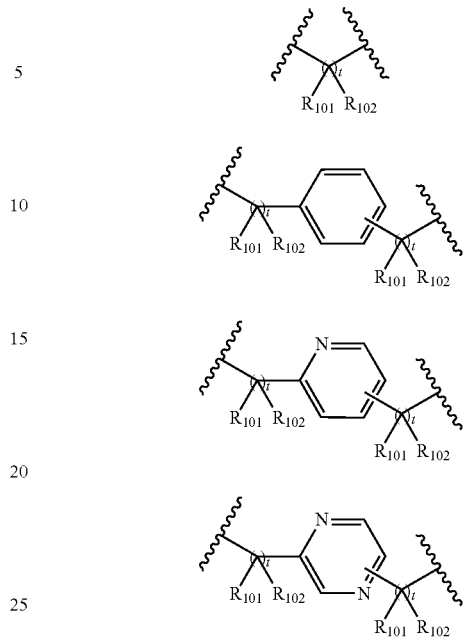

wherein each t is independently 0, 1, 2, 3, 4, 5, 6, 7, 8, 9, 10, 11, 12, 13, 14, 15, 16, 17, 18, 19, 20, 21, 22, 23 or 24;

i is 1, 2, 3, 4, 5 or 6;

j is 0, 1, 2, 3, 4, 5, 6, 7, 8, 9 or 10;

u is an integer between 1 and 500 or between 1 and 10 or between 1 and 20 or between 1 and 100 or between 1 and 300;

each $R_{101}$ and $R_{102}$ is independently selected from hydrogen, halogen, —$OR_{20}$, —$SR_{20}$, —$NR_{20}R_{21}$, —$CF_3$, —CN, —$NO_2$, —$N_3$, —$C(O)OR_{20}$, —$C(O)R_{20}$, —$C(O)NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl —$S(O)_2R_{100}$, —$S(O)_3R_{100}$, —$S(O)_3H$, alternatively, two $R_{101}$ and $R_{102}$ groups together with the atom or atoms to which they are attached may form one, two or three rings with optional additional substitution.

In a preferred embodiment, $G_1$ is selected from Table C:

TABLE C

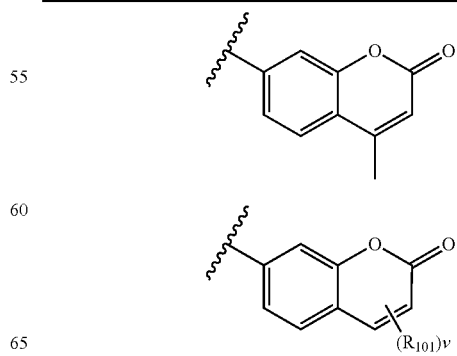

TABLE C-continued
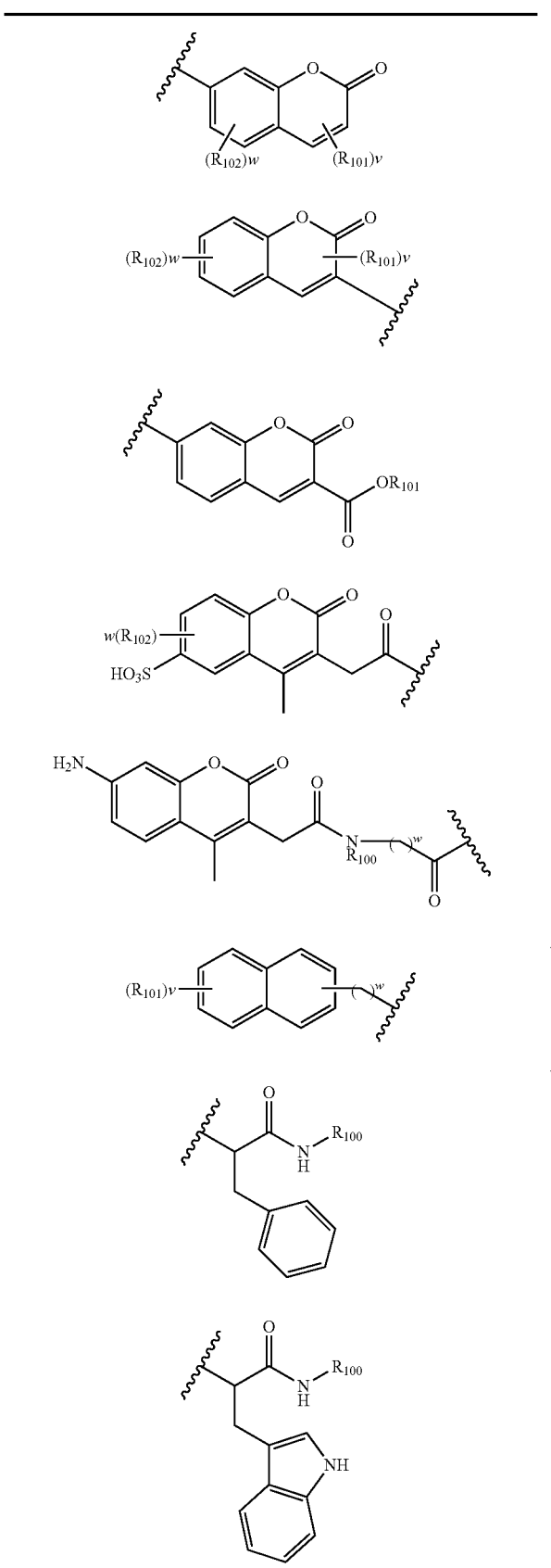
TABLE C-continued
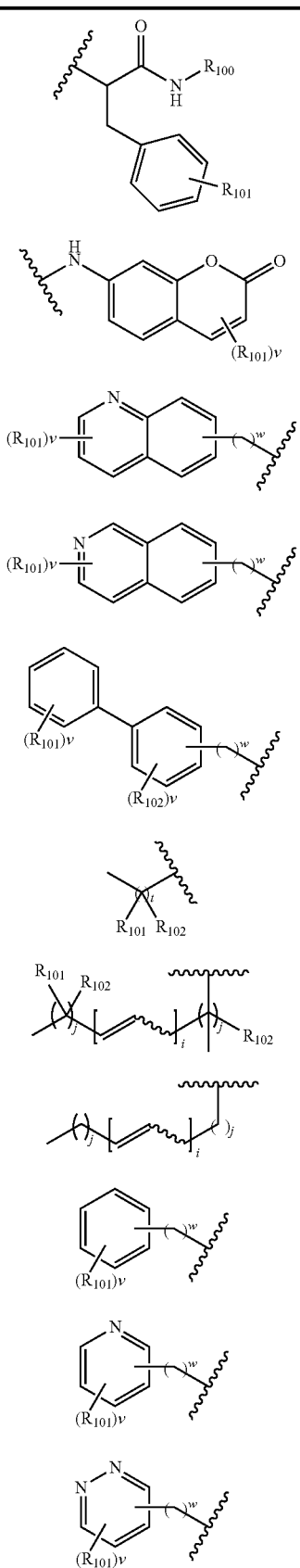

TABLE C-continued

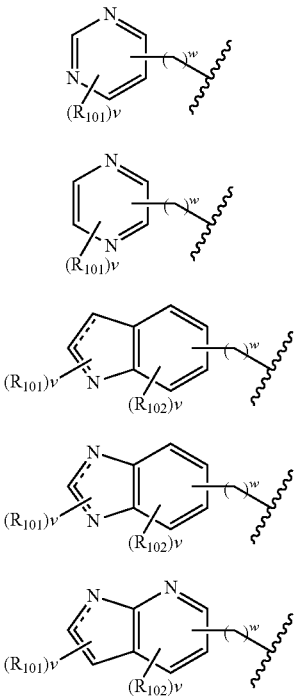

wherein each $R_{101}$ and $R_{102}$ is independently selected from hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl —S(O)$_2R_{100}$, —S(O)$_3R_{100}$, —S(O)$_3$H;

wherein each $R_{20}$ and $R_{21}$ is independently hydrogen, aliphatic, substituted aliphatic, aromatic or substituted aromatic;

alternatively, two $R_{101}$ and $R_{102}$ groups together with the atom or atoms to which they are attached may form one, two or three rings with optional additional substitution; and, each v and w is independently 0, 1, 2, 3 or 4.

The invention further relates to a method for determining lysine deacetylase activity of a protein or peptide comprising the step of incubating said protein or peptide with a compound according to Formula I and monitoring the modification of a lysine residue of said compound of Formula I over time. The compounds of Formula I can be used to determine the activity of HDAC isoforms 1, 2, 3, 4, 5, 6, 7, 8, 9, 10, 11 or SIRT 1, 2, 3, 4, 5, 6 or 7. In one embodiment, these substrates allow the measurement of activity of full length or truncated variants of histone deacetylases (HDAC 1-11 or SIRT 1-7) and their corresponding complexes with microfluidic lab-on-chip technology. In addition, these substrates can be used for screening HDAC inhibitors, studying mechanism of inhibition and profiling their selectivity.

The invention further relates to a method for assessing acetylation or deacetylation activity in a cell line, comprising the steps of: (i) providing a first and second cell lines having histone deacetylase or one or more Sirtuin activity; (ii) contacting said first cell line with an inhibitor of one or more isoforms of HDAC or Sirtuin; (iii) wherein said second line is not contacted with an inhibitor of HDAC or Sirtuin; (iv) incubating said first and second cell lines with one or more isoforms of HDAC or Sirtuin; and, assessing the level of acetylation in said first and second cell lines: and comparing the levels of acetylation of first cell line with the acetylation of a second cell line.

In one embodiment, the invention relates to a compound of Formula II:

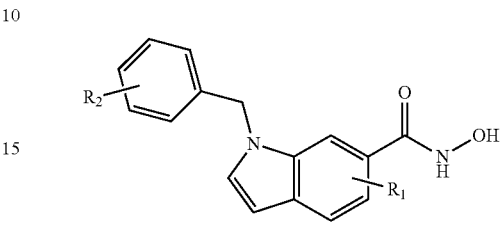

wherein $R_1$ is selected from halogen, $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkynyl and substituted $C_1$-$C_6$ alkynyl; and, $R_2$ is selected from —O—$C_1$-$C_6$ alkyl, substituted —O—$C_1$-$C_6$ alkyl, —$SC_1$-$C_6$ alkyl and substituted —$SC_1$-$C_6$ alkyl.

In a preferred embodiment, the compound of Formula II is selected from:

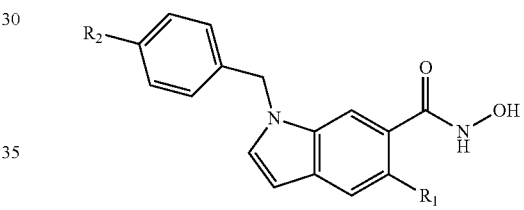

wherein $R_1$ is F, Cl, I, methyl, ethyl, propyl, isopropyl, n-butyl, t-butyl and $CF_3$; and $R_2$ is —$OCH_3$ or —$OCH_2CH_3$.

In a preferred embodiment the compound of Formula II is:

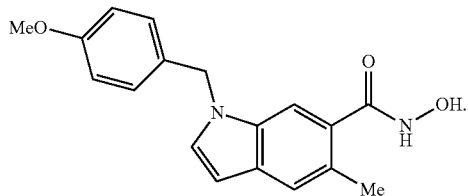

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g., single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g., pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g., morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g., $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

EXAMPLES, METHODS AND DISCUSSION

Figure 1:
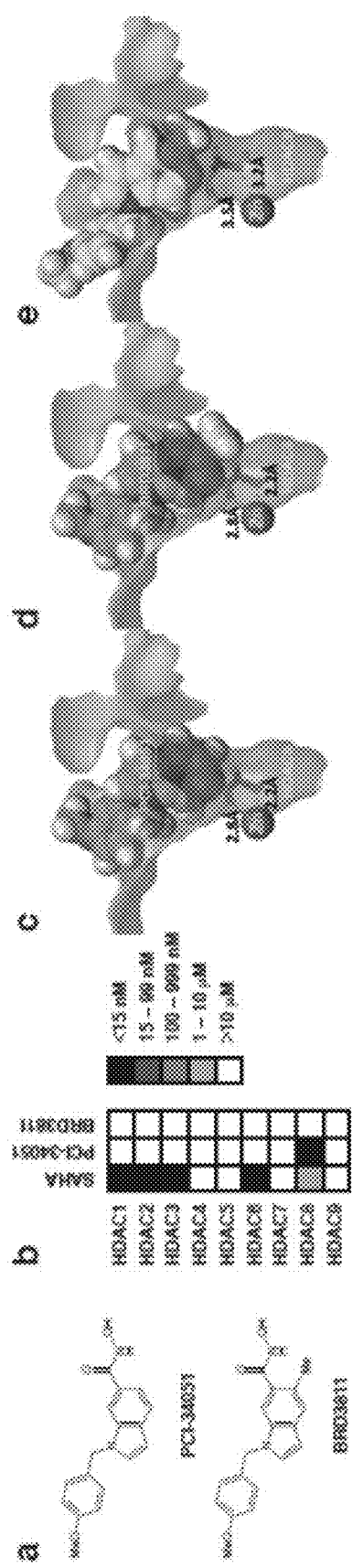
FIG. 1. Chemical tools for studying HDAC8. (a) Chemical structures of the isoform selective HDAC8 inhibitor PCI-34051 and the structurally related negative control compound BRD3811. (b) HDAC inhibitor potencies for PCI-34051, BRD3811, and the non-selective HDAC inhibitor SAHA. (c) PCI-34051 docked into a crystal structure of HDAC8 (PDB code 1T64). (d) Replacement of the ortho-hydrogen in the docked structure of PCI-34051 (c) with a methyl group. The methyl group protrudes from the enzyme pocket. (e) BRD3811 docked into a crystal structure of HDAC8 (PDB code 1T64).

To elucidate the cellular substrates and better define the biology of HDAC8, we undertook an unbiased, chemical biology approach that involved monitoring global acetylation and gene expression changes in a representative cell line following treatment with a known, potent, and highly selective small molecule inhibitor of HDAC8. Small molecule modulation coupled with mass spectrometry offers distinct advantages for the identification of acetylation substrates and specific lysine sites responsive to HDAC8 relative to protein knockdown, knockout, or pulldown approaches, including: 1) de-convolution of catalytic vs. scaffolding functions associated with HDACs, (You, S.-H., Lim, H. W., Sun, Z., Broache, M., Won, K. J., Lazar, M. A. (2013) Nuclear receptor co-repressors are required for the histone-deacetylase activity of HDAC3 in vivo. *Nat. Struct. Mol. Biol.* 20, 182-187); 2) temporal control; 3) increased resolution and sensitivity; and 4) the avoidance of complications associated with transient and/or metastable interactions and complexes. Therefore, we focused on using the highly selective and potent HDAC8 inhibitor, PCI-34051 (Balasubramanian, A., Ramos, J., Luo, W., Sirisawad, M., Verner, E. Buggy, J. J. (2008) *Leukemia* 22, 1026-1034) as well as a suitably designed negative control compound to account for potential compound-driven off-target effects (FIG. 1a, b). The inclusion of a negative control compound was particularly important, as PCI-34051 contains a metal-chelating hydroxamic acid group, and this motif has the potential to bind a variety of metalloenzymes. As such, we designed and synthesized BRD3811 (FIG. 1a), a compound that retains the hydroxamic acid functionality and contains a minor structural modification to PCI-34051 (i.e., a single methyl group introduced ortho to the hydroxamic acid group) resulting in a 1,000-fold reduction in potency for inhibition of HDAC8 (FIG. 1b). Consistent with this finding, molecular docking of PCI-34051 (FIG. 1c) and BRD3811 (FIG. 1e) into the active site of an HDAC8 crystal structure (PDB accession code 1T64) reveals that the methyl group of BRD3811 cannot be accommodated in the catalytic binding domain of HDAC8 while maintaining an optimal zinc chelation geometry.

Figure 2:
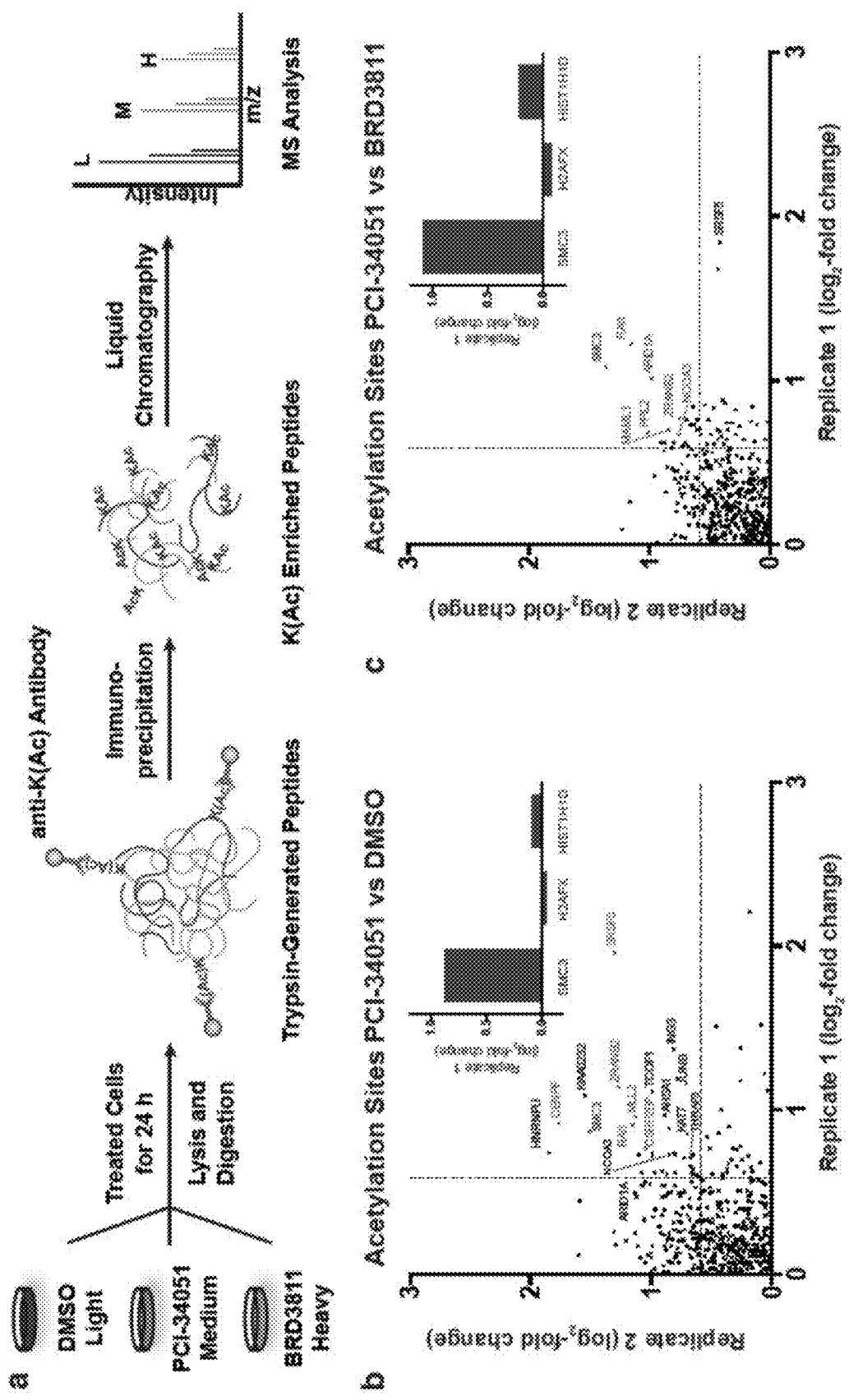
FIG. 2. Identifying novel substrates of HDAC8. (a) Schematic of experimental design. (b) Acetylated proteins regulated by treatment with PCI-34051 as compared to DMSO or (c) BRD3811 as the control. Each axis represents a single replicate and denotes $\log_2$-fold changes in acetylation with dashed lines indicating a 1.5-fold change in acetylation. Proteins that passed a p-value cutoff of ≤0.05 in both replicates and were not regulated by the negative control compound BRD3811 are highlighted in red. Insets show $\log_2$-fold changes in acetylation for select examples of replicate 1 and emphasize the relative lack of histone acetylation by comparison to SMC3 for each experiment. (d) Tables depicting acetylation sites regulated by more than 1.5-fold and passing p-value cutoffs of 0.05 in both replicates when PCI-34051 treatment was compared to DMSO or to (e) BRD3811 treatment as the control. (f) Steady state kinetic parameters (±standard error) for the deacetylation of synthetic acetylated peptides corresponding to a subset of identified HDAC8 substrates. Reactions were catalyzed by bacterially expressed human Zn-bound HDAC8 (see methods). (g) Dependence of Zn-HDAC8-catalyzed deacetylation on the concentration of the ARID1A peptide. The Michaelis-Menten equation is fit to the data.
Figure 2:
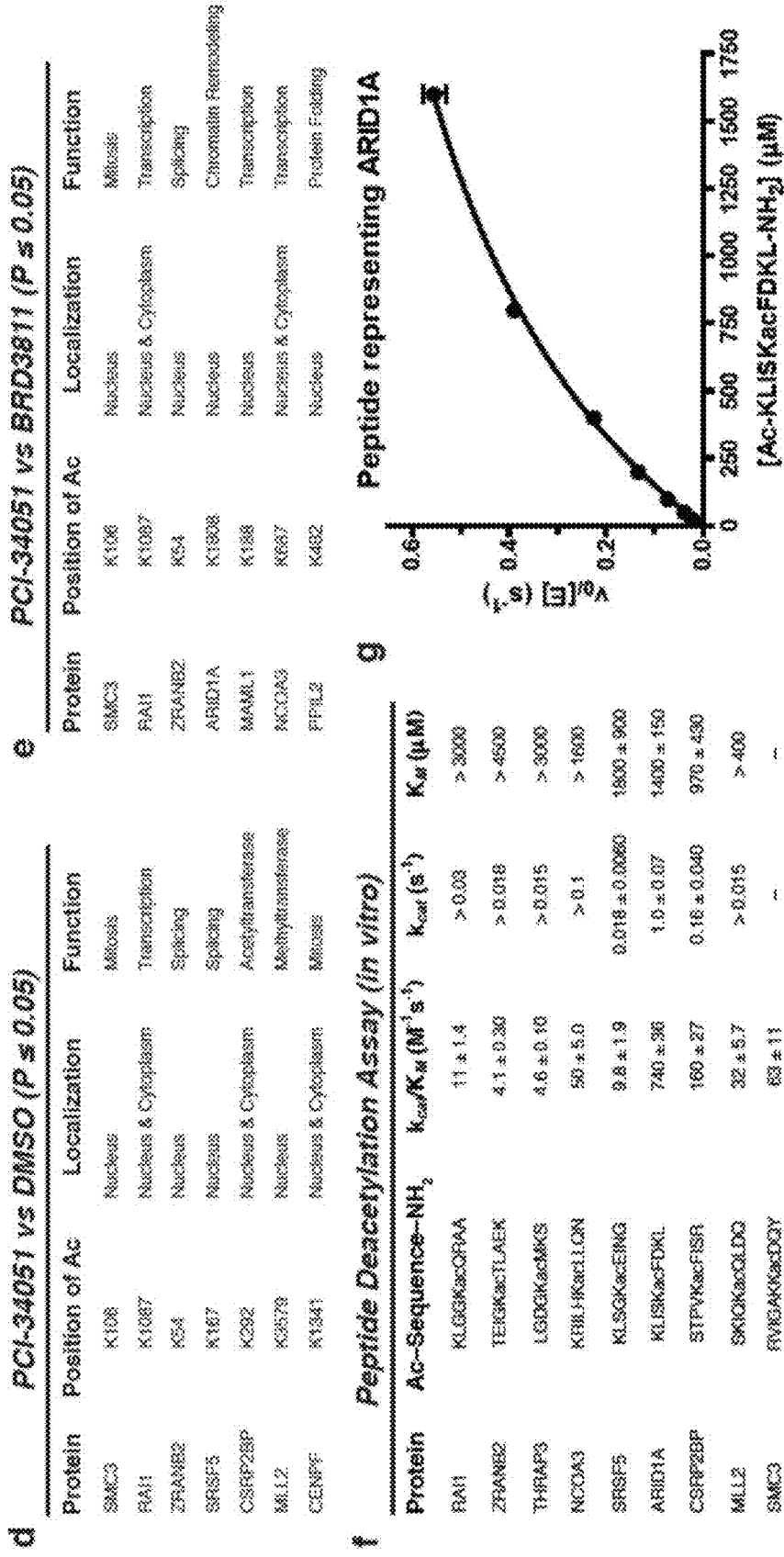

Using these chemical tools, we compared the changes in global acetylation in a representative cell line known to express HDAC8 (i.e. MCF7) after treatment with each compound using Stable Isotope Labeling of Amino Acids in Cell Culture (SILAC)-based quantitative mass spectrometry (MS). (Ververis, K., Karagiannis, T. C. (2012) An atlas of histone deacetylase expression in breast cancer: fluorescence methodology for comparative semi-quantitative analysis. *Am. J. Transl. Res.* 4, 24-43). Briefly, cells were grown in the presence of light, medium, or heavy arginine and lysine followed by treatment with either PCI-34051 (10 µM), BRD3811 (10 µM), or vehicle (DMSO) for 24 hours (FIG. 2a). Global acetylation profiling was completed by digesting cellular proteins with trypsin and enriching the acetylated peptides by immunoprecipitation using an antibody specific for acetylated lysine residues.

Figure 6:
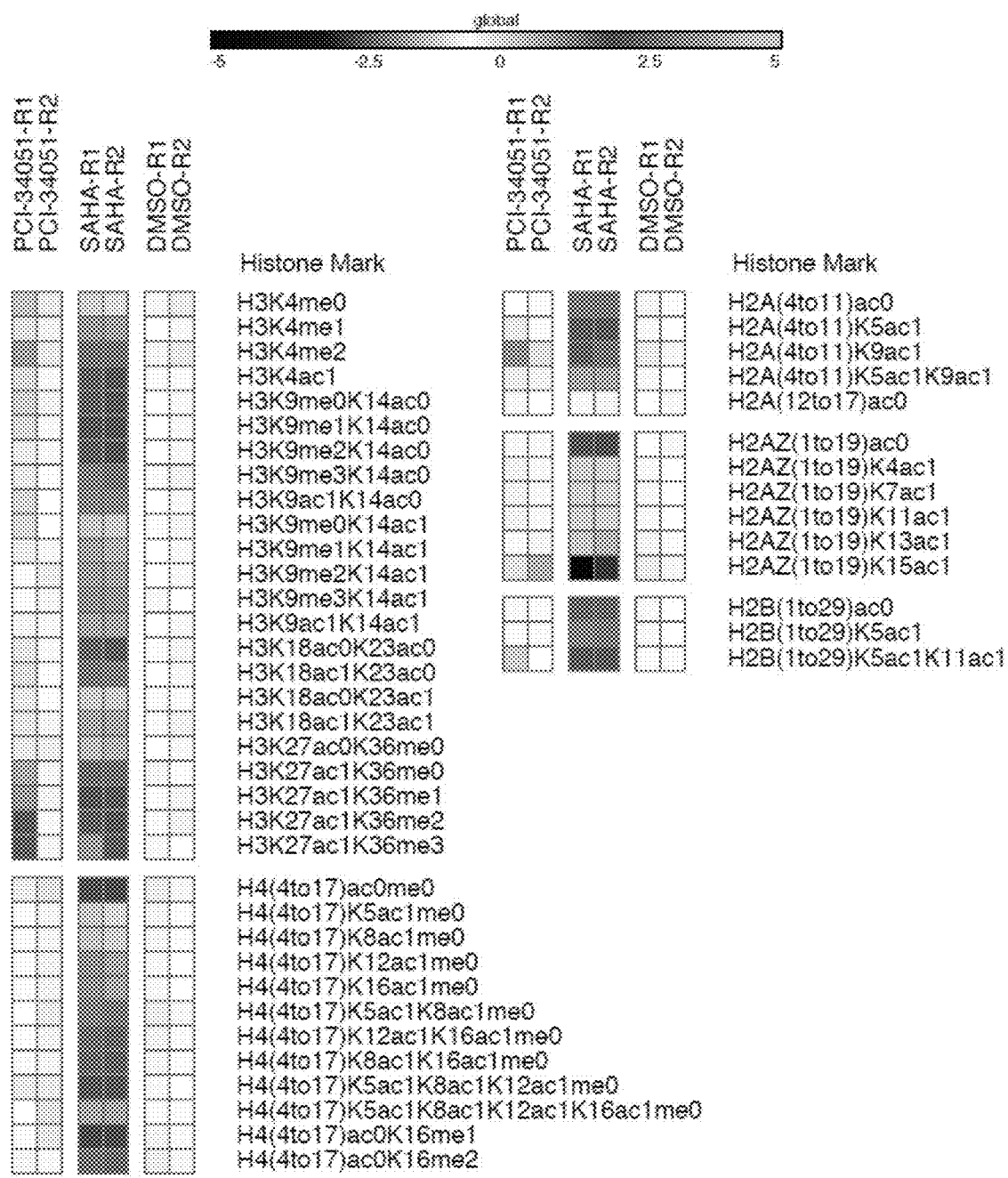
FIG. 6: Histone acetylation is not altered by treatment with PCI-34051. Each row represents a unique combination of histone modifications (as denoted by "Histone Mark") and each column represents a treatment of MCF-7 cells with the compound indicated at 10 µM for 24 h. Each compound treatment was performed in biological duplicate (R1 and R2). Each cell is colored by the $log_2$-fold change over the average of the DMSO replicates as denoted in the scale bar. Global histone profiles were obtained in a manner essentially equivalent to a previous report. (Kim, J. H., Yu, S., Chen, J. D., Kong, A. N. (2013) The nuclear cofactor RAC3/AIB1/SRC-3 enhances Nrf2 signaling by interacting with transactivation domains. *Oncogene* 32, 514-527).

This approach enabled us to identify numerous protein sites whose acetylation increased by more than 1.5-fold in each of two replicates upon treatment with PCI-34051 relative to DMSO (FIG. 2b). Of these, 7 passed a p-value cutoff of ≤0.05 (FIG. 2b, red; FIG. 2d) and were not regulated greater than 1.5-fold upon treatment with negative control compound BRD3811 relative to DMSO (Table 1 and FIG. 6). Alternatively, a direct comparison of PCI-34051 treatment to BRD3811 treatment (FIG. 2c) revealed 22 protein sites whose acetylation increased by more than 1.5-fold with 7 passing a p-value cutoff of ≤0.05 in two replicates (FIG. 2c, red; FIG. 2e). From these data sets, we deemed 5 proteins (i.e., SMC3, RAI1, ZRANB2, NCOA3, and THRAP3) to be high-confidence substrates for HDAC8 as they were regulated by 1.5-fold or greater when PCI-34051 treatment was compared to both DMSO as well as to the negative control compound. Furthermore, ARID1A and SRSF5 were also considered candidate substrates for HDAC8 as they narrowly fell outside the bounds of our arbitrary cutoffs (i.e., 1.5-fold change and p-value ≤0.05) in only one of four experiments.

Our unbiased approach successfully identified SMC3, a known substrate of HDAC8, as being significantly regulated by treatment with the HDAC8-selective inhibitor and not BRD3811. (Deardorff, M. A. et al., (2012) HDAC8 mutations in Cornelia de Lange syndrome affect the cohesin acetylation cycle. *Nature* 489, 313-317). Furthermore, we were able to demonstrate that HDAC8-mediated deacetylation occurs on K106 of SMC3, one of two sites known to be acetylated by the acetyltransferase ESCO 1. (Zhang, J., Shi, X., Li, Y., Kim, B. L., Jia, J., Huang, Z., Yang, T., Fu, X., Jung, S. Y., Wang, Y., Zhang, P., Kim, S. T., Pan, X., Qin, J. (2008) Acetylation of Smc3 by Eco1 is required for S phase sister chromatid cohesion in both human and yeast. *Mol. Cell* 31, 143-151). Our coverage of acetylated proteins did not include ERR-α, the only other known cellular HDAC8 substrate; and therefore, we cannot verify its regulation by HDAC8 in MCF7 cells. Our coverage did include several histone proteins, and we did not observe any significant changes in histone acetylation status upon treatment with PCI-34051 when compared to DMSO or BRD3811. Changes in H2A (H2AFX) and H1.3 (HIST1H1D) acetylation relative to SMC3 are shown for comparison (FIGS. 2b and 2c, insets).

Figure 5:
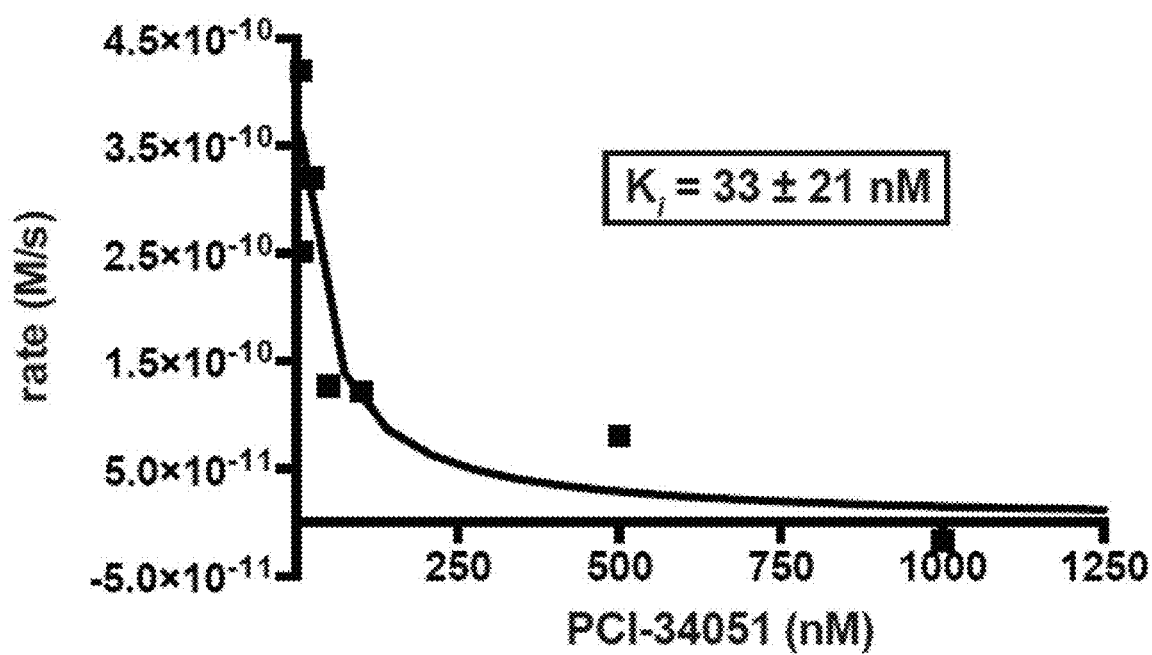
FIG. 5: PCI-34051 potently inhibits the HDAC8-catalyzed in vitro deacetylation of a peptide corresponding to acetylated ARID1A. The value of the inhibition constant (Ki) for PCI-34051 was measured from the dependence of the deacetylation activity at various inhibitor concentrations measuring the formation of acetate using an enzyme-coupled assay. The reaction contained recombinant Zn(II)-HDAC8 (5 nM) and Ac-KLISKacFDKL-NH2 (peptide corresponding to ARID1A, 100 µM) in assay buffer (2.7 mM KCl, 137 mM NaCl, 50 mM HEPES, pH 7.8, 0.001% BSA, 0.001% Tween 20).

To further validate the substrates identified in our proteomics experiments, we devised in vitro enzymatic deacetylation experiments using recombinant human HDAC8 and synthetic acetylated peptides (8-10 AA) based on the sequences of our candidate substrates. Our peptide design centered on the identified lysine (K) acetylation sites, ensuring that the regulated lysines were flanked on either side by several residues. These "artificial" substrates were incubated with HDAC8 and deacetylation was measured from the production of acetate using an enzyme-coupled assay to determine the steady state kinetic parameters (FIG. 2f and methods section). Human Zn-HDAC8 catalyzed the deacetylation of all these synthetic peptides in vitro (FIG. 2f), albeit with catalytic efficiencies ($k_{cat}/K_M$) ranging across three orders of magnitude. Four of the peptides assayed (i.e., NCOA3, ARID1A, CSRP2BP, and MLL2) have values of $k_{cat}/K_M$ within a factor of 2 or higher than the peptide corresponding to SMC3, providing further evidence that these proteins are likely HDAC8 substrates. In particular, the peptide corresponding to ARID1A is the most efficient non-fluorophore conjugated peptide substrate of Zn-HDAC8 discovered to date ($k_{cat}/K_M$=740 $M^{-1}s^{-1}$) (FIGS. 2f and g). (Madsen, A. S., Olsen, C. A. (2012) Profiling of substrates for zinc-dependent lysine deacylase enzymes: HDAC3 exhibits decrotonylase activity in vitro. *Angew. Chem. Int. Ed.* 51, 9083-9087). Consistent with previous work, peptides containing an aromatic residue adjacent to the target lysine (e.g., those corresponding to ARID1A and CSRP2BP) are preferred substrates of HDAC8. (Wolfson et al.). To further characterize the enzyme specificity of these synthetic substrates, we profiled the deacetylation activity of commercially available, human recombinant HDACs 1-9 (FIG. 10). While multiple isozymes catalyzed deacetylation of all of the putative substrates, no single peptide was recognized by all of the HDACs tested, and none were uniquely deacetylated by HDAC8. However, the ARID1A peptide exhibited the largest $k_{cat}/K_M$ values for HDAC8 and HDAC3's closest homologue, HDAC3, with values of 2400 and 2500 $M^{-1}s^{-1}$, respectively (FIG. 10). (Gregoretti, I. V., et al.). Finally, we determined the deacetylase inhibitory activity of PCI-34051 towards the ARID1A peptide substrate using commercially available human HDAC8 and calculated a $K_i$ value of 33 nM, demonstrating the ability of this molecule to inhibit HDAC8 in a manner consistent with our cell-based observations (FIG. 5).

Figure 8:
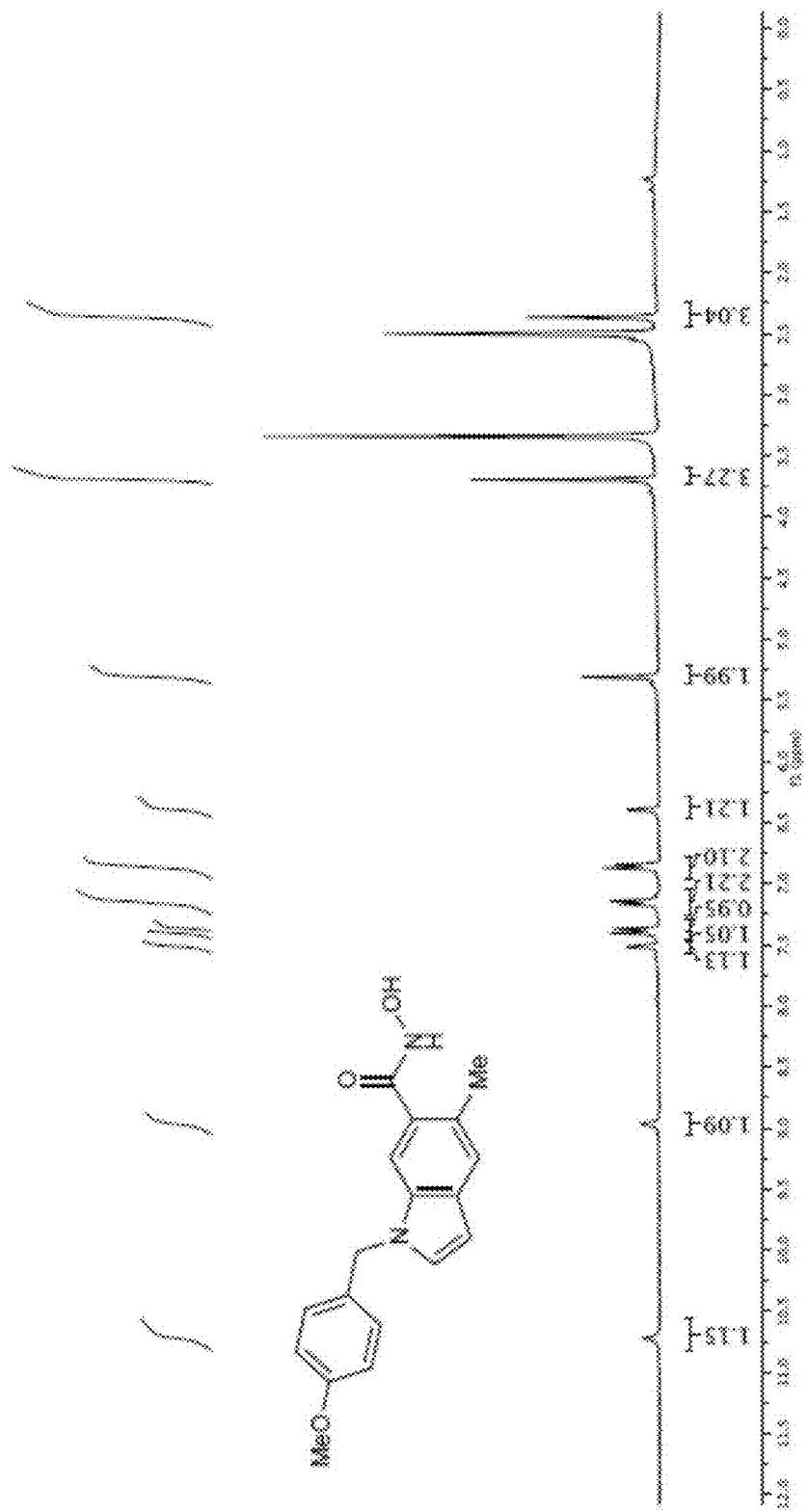
FIG. 8: Characterization data confirming the identity and purity of BRD3811. (a) 1H NMR of BRD3811 in DMSO-d6.
Figure 8:
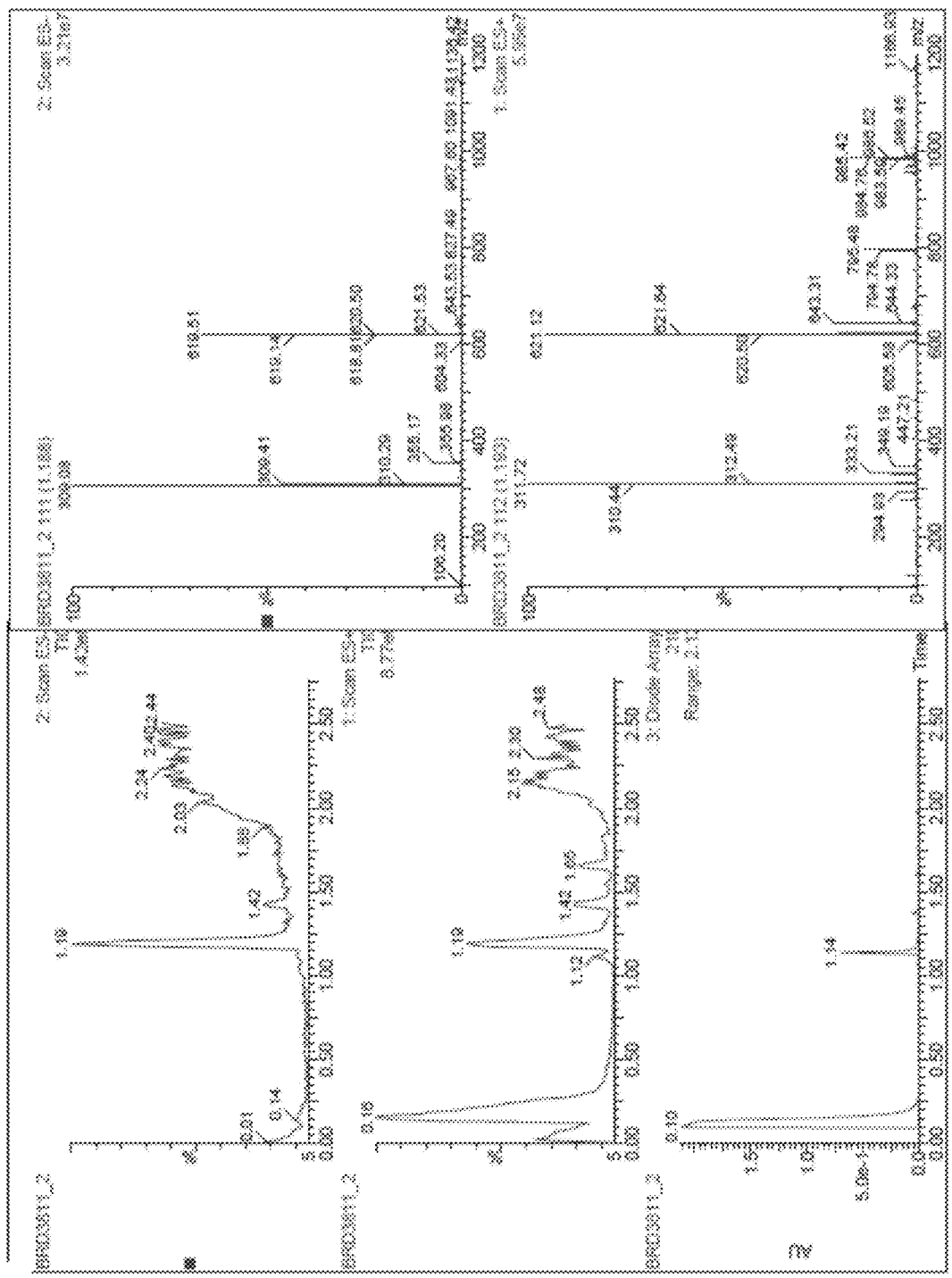

Most of the substrates identified in our study are localized in the nucleus (FIGS. 2d and e) and include transcription factors as well as proteins intimately involved in epigenetic regulation, chromatin remodeling, or RNA splicing. Interestingly, histone proteins were not identified as substrates in our acetylome profiling experiments, and this fact was later confirmed in separate, targeted SILAC experiments designed to specifically monitor for histone acetylation changes (FIG. 8). These results are consistent with previous reports. (Suzuki, T., Ota, Y., Masaki, R., Bando, M., Gotoh, A., Itoh, Y., Tsumoto, H., Tatum, P. R., Mizukami, T., Nakagawa, H., Iida, S., Ueda, R., Shirahige, K., Miyata, N. (2012) Rapid discovery of highly potent and selective inhibitors of histone deacetylase 8 using click chemistry to generate candidate libraries. *J. Med. Chem.* 55, 9562-9575; Suzuki, T., Muto, N., Bando, M., Itoh, Y., Maski, A., Ri, M., Ota, Y., Nakagawa, H., Iida, S., Shirahige, K., Miyata, N. (2014) Design, synthesis, and biological activity of NCC149 derivatives as histone deacetylase 8-selective inhibitors. *ChemMedChem.* 9, 657-664). Intrigued by the non-histone but primarily nuclear nature of the candidate substrates, we tested if HDAC8 inhibition could lead to changes in gene expression independent of changes in histone acetylation. To this end, we measured the expression changes in MCF7 cells of approximately 1,000 landmark genes (L1000) as a representative measure of genome-wide effects upon treatment with PCI-34051 or BRD3811 across the dose range of 0.04 M-10 M (see methods). We then selected the dose-responsive genes using the IsoGene package (Pramana, S., Lin, D., Haldermans, P., Shkedy, Z., Verbeke, T., Göhlmann, H., De Bondt, A., Talloen, W., Bijnens, L. (2010) IsoGene: An R package for analyzing dose-response studies in microarray experiments. *The R Journal* 2, ISSN 2073-4859) (http://CRAN.R-proiect.org/package=IsoGene). PCI-34051 altered the expression of significantly more genes (70 genes, than did BRD3811 (Appendix 2: 11 genes, Supplementary Table 5). While several genes, such as HMOX1, were differentially regulated by both PCI-34051 and BRD3811, the magnitude of the change was much greater for the PCI-34051 treatment.

Figure 3:
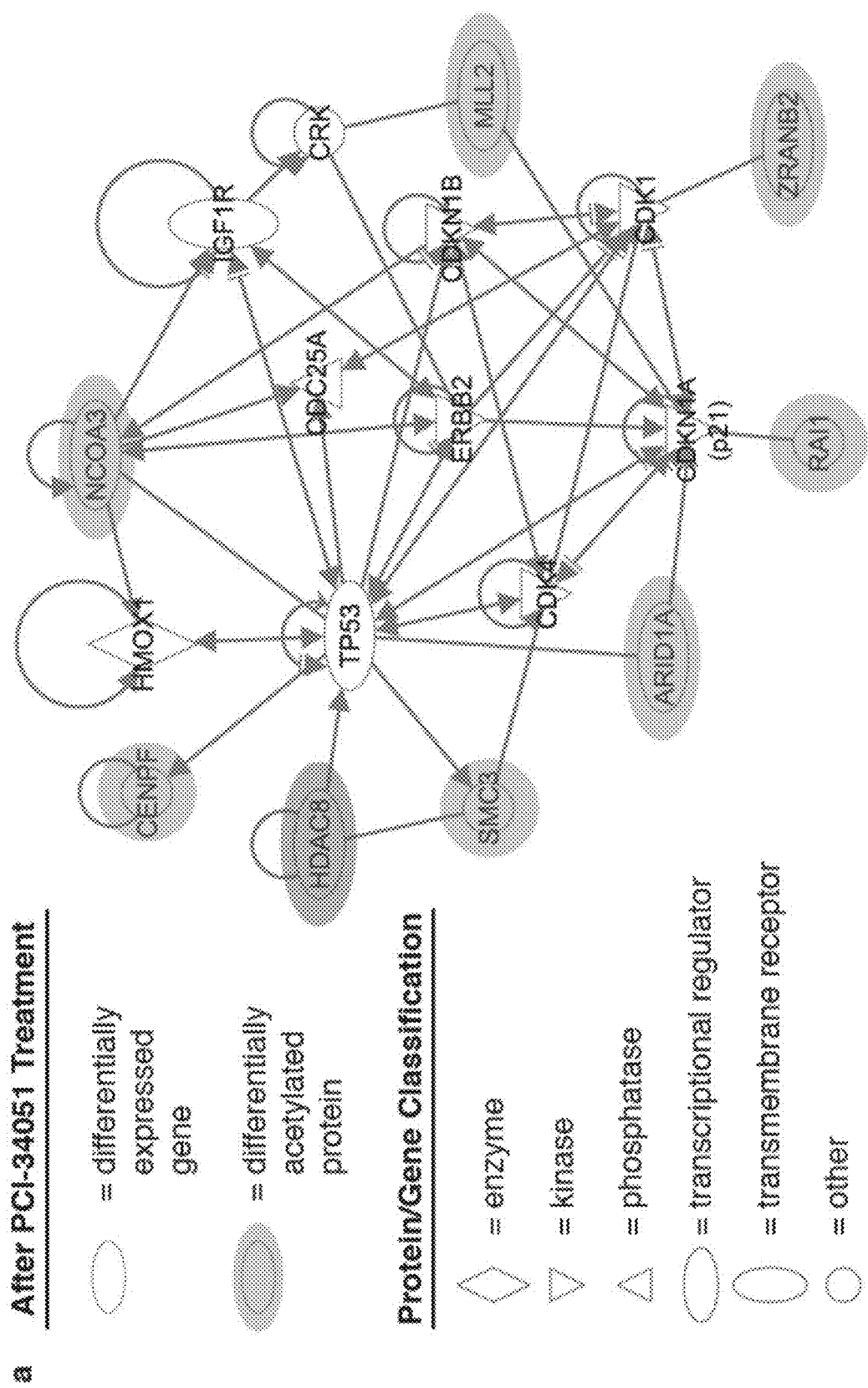
FIG. 3. Pathway analysis of candidate HDAC8 substrates. (a) A connection network was generated with Ingenuity Pathways Analysis (INGENUITY® Systems, www.ingcnuity.com), using HDAC8 and the proteins differentially acetylated and expressed, respectively, upon treatment with PCI-34051 as inputs. Only those proteins or genes with known connections to other proteins or genes in the pathway are shown. HDAC8 is highlighted in a blue ellipse, while red ellipses denote proteins differentially acetylated upon treatment with PCI-34051. The remaining nodes represent genes differentially expressed upon treatment with PCI-34051. Relationships indicated by lines in this graph are found by INGENUITY® and can include protein-protein interactions, transcriptional regulation, co-expression, activation, binding, phosphorylation, inhibition, protein-DNA interactions, binding regulation, localization, molecular cleavage, and translocation. These relationships can be between two molecules (straight arrows) or between a molecule and itself (curved arrows), as in the case of auto-phosphorylation for example. (b) Treatment with PCI-34051 for 24 h results in a dose-dependent increase in p21 expression. (c) Representative western blot after treatment of MCF7 cells with either PCI-34051 or BRD3811 at 10 M for 48 h shows that PCI-34051, but not the negative control, induces an increase in p21 protein levels. (d) Quantitation of western blot data from 4 independent experiments. The star denotes P≤0.05, relative to DMSO, as determined by a one-way analysis of variance (ANOVA) utilizing a post-hoc Dunnett's multiple comparison's test.
Figure 3:
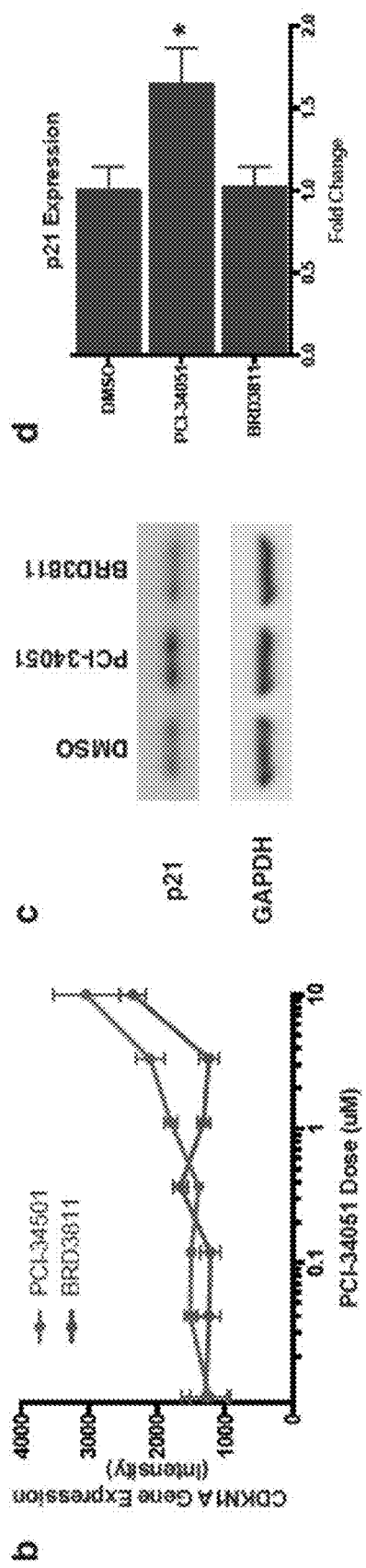
Figure 4:
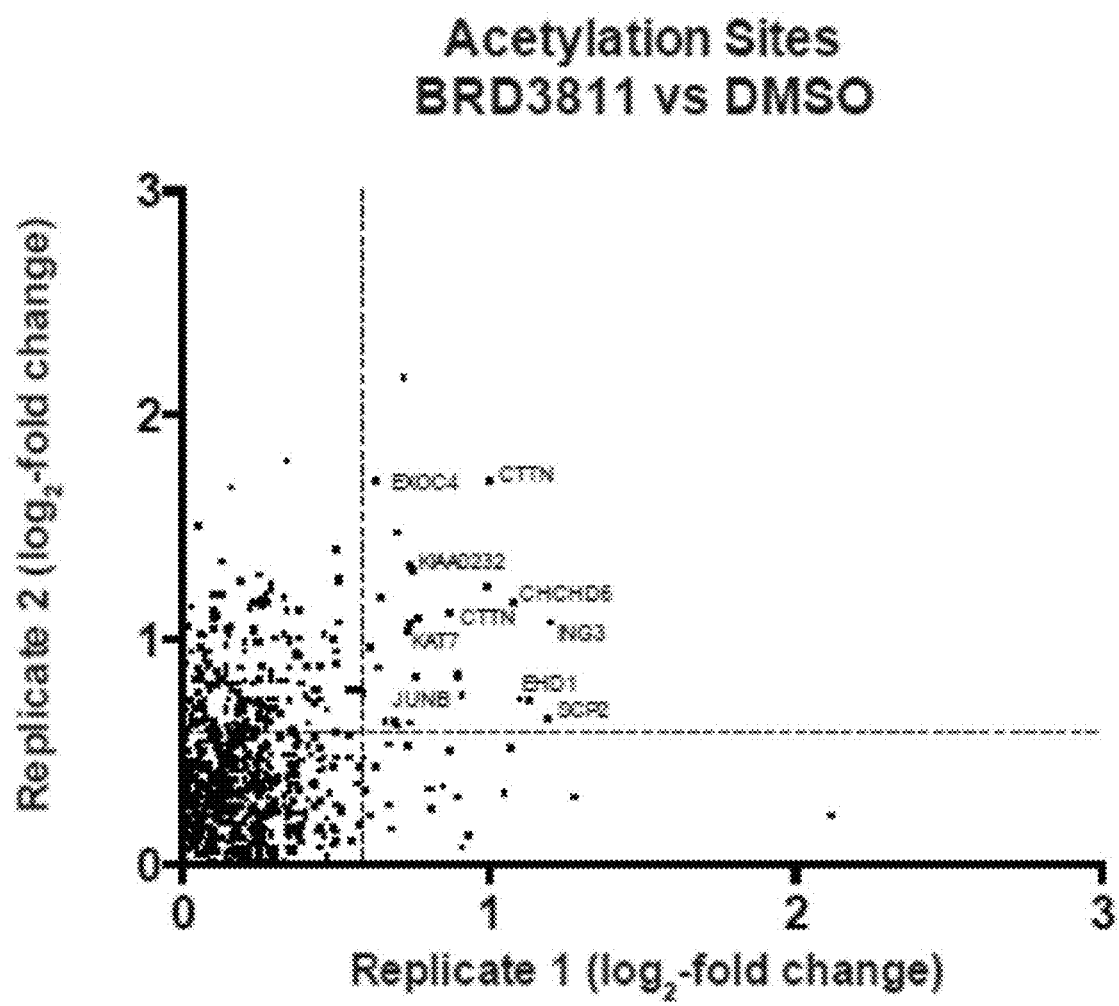
FIG. 4: Treatment with BRD3811 induces changes in protein acetylation. Axes represent log 2-fold changes in acetylation for two independent experiments. Dashed lines denote a 1.5-fold change. Representative examples of proteins whose acetylation was regulated by more than 1.5-fold in each of two replicates are highlighted.

In an attempt to connect the modulated transcripts to our candidate HDAC8 substrates, we searched for known biological pathway connections between our high-confidence HDAC8 substrates (FIGS. 2d and 2e) and the 70 genes dose-responsive to PCI-34051 treatment (Appendix 1: Supplementary Table 4) using the INGENUITY® IPA Knowledge Base (FIG. 3a). No direct associations between HDAC8 and the newly identified substrates were found; however, both the known HDAC8 substrate SMC3 and the tumor suppressor p53 (TP53) were directly connected to HDAC8. Our acetylome coverage did not include p53, therefore we were unable to determine whether it can be directly modified by HDAC8. Several of the newly identified acetylation substrates were directly linked to genes differentially expressed upon inhibition of HDAC8. NCOA3, a protein known to positively regulate the expression of HMOX1, is one such example. (Kim, J. H., Yu, S., Chen, J. D., Kong, A. N. (2013) The nuclear cofactor RAC3/AIB1/SRC-3 enhances Nrf2 signaling by interacting with transactivation domains. *Oncogene* 32, 514-527). Additionally, we found that 3 of the newly identified substrates (i.e., ARID1A, RAI1, and MLL2) were directly linked to the cell cycle regulator p21 (CDKN1A). This led us to speculate that the increased expression of p21 observed upon treatment with PCI-34051 could be driven in part by the acetylation changes of ARID1A. Alternatively, increased acetylation of RAI1 and/or MLL2 could influence the regulation of this important gene. Many HDAC inhibitors are known to cause the upregulation of p21, but until now, the exact substrates responsible for mediating that effect have remained obscure. (Sun, Z., Feng, D., Fang, B., Mullican, S. E., You, S. H., Lim, H. W., Everett, L. J., Nabel, C. S., Li, Y., Selvakumaran, V., Won, K. J., Lazar, M. A. (2013) Deacetylase-independent function of HDAC3 in transcription and metabolism requires nuclear receptor corepressor. *Mol. Cell* 52, 769-782). When MCF7 cells are treated with PCI-34051 over the dose range 0.04 μM-10 μM, a dose-dependent increase in the level of the p21 transcript is observed (FIG. 3b). Conversely, BRD3811 increased the level of p21 transcript only at the highest dose tested (i.e., 10 μM) (FIG. 3b). To further validate this finding, we examined changes in p21 protein levels after treatment with each compound, and PCI-34051 treatment (10 μM) increased p21 (visualized via western blot) while BRD3811 (10 μM) treatment did not (FIGS. 3c and d).

Figure 7:
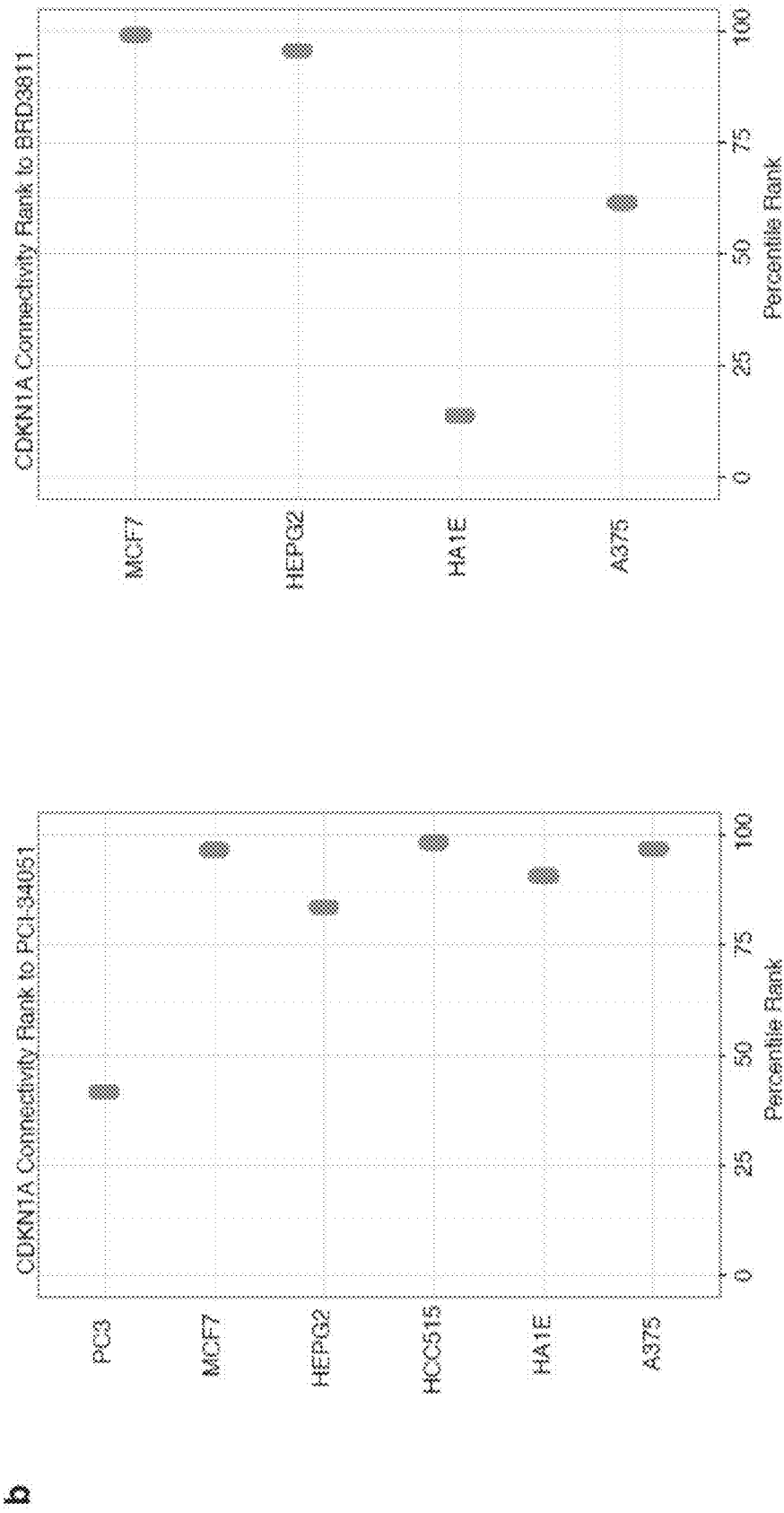
FIG. 7: PCI-34051 treatment is highly correlated with p21 (CDKN1A) overexpression. (a) Average percentile rank by gene expression signature similarity across multiple cell types. Treatment with PCI-34051 is highly correlated with p21 (CDKN1A) overexpression (96th percentile on average) while treatment with BRD3811 is not (66 percentile on average). Percentile ranks are relative to a total of 430 overexpressed genes. (b) PCI-34051 treatment produced a replicable expression signature in 6 cell lines while BRD3811 treatment was replicable in only 4. For the cell lines in which the compound treatments were reproducible, PCI-34051 treatment was more similar to p21 overexpression than was BRD3811 treatment.

To assess whether our findings extend beyond the context of a single cell type and to incorporate into our analysis orthogonal biological perturbations, we expanded our gene expression studies using L1000 into several cell lines representative of distinct tissue types: PC3 (prostate), HEPG2 (liver), HCC515 (lung), HA1E (kidney), A375 (skin), A549 (lung), HT29 (colon). We then created a gene expression signature using the 1,000 landmark genes, and compared PCI-34051 and BRD3811 treatments to the signatures of other bioactive perturbagens using the connectivity map (Cmap) database (www.broadinstitute.org/cmap/) as previously described (see methods). We integrated the results of multiple independent Cmap queries using the cell lines highlighted above, and we observed that PCI-34051 treatment was highly correlated with the overexpression of p21 across multiple cell lines while BRD3811 treatment was not (FIG. 7). In fact, p21 overexpression was the overexpression perturbation most highly correlated with PCI-34051 treatment, ranking in the $96^h$ percentile on average (BRD3811 treatment did not correlate well with p21 overexpression, $66^h$ percentile rank). It is quite attractive to speculate that some of the anti-cancer effects of the HDAC8 inhibitor PCI-34051[19] are mediated in part by increasing p21 levels through these newly discovered substrates. These candidate substrates of HDAC8 may provide a more targeted approach toward specific cancers (or other diseases) driven by the dysregulation of proteins and/or genes within this HDAC8 network. In the case of ovarian clear cell carcinoma, mutations in ARID1A are found in almost half of all cases and it has been demonstrated that in frame indel mutations fail to induce p21 expression through increased degradation in the nucleus or decreased promoter binding. (Guan, B., Gao, M., Wu, C.-H., Wang, T.-L., Shih, l.-M. (2012) Functional analysis of in-frame indel ARID1A mutations reveals new regulatory mechanisms of its tumor suppressor functions. *Neoplasia* 14, 986-993A). Efforts toward defining the functional consequences of the change in acetylation of these proteins by HDAC8 are ongoing.

In conclusion, we have identified several novel substrates of HDAC8 by taking an unbiased approach coupling chemical tools with acetylome profiling. The proteins identified include the known HDAC8 substrate SMC3, but do not include histones. Furthermore, these candidate substrates were predominantly nuclear and involved in a diverse range of cellular functions including transcription and RNA splicing. We demonstrated through in vitro enzymatic assays as well as through gene and protein expression studies that inhibition of HDAC8 can affect acetylation status ultimately influencing the levels of downstream proteins. Our experimental design relied on using BRD3811, a negative control compound based on the structure of the potent and selective HDAC8 inhibitor PCI-34051. Our approach represents a general strategy that should prove useful in future studies aimed at the identification of the endogenous substrates of other members of the HDAC family of enzymes.

Synthesis of BRD-3811: PCI-34051 is commercially available. BRD3811 was synthesized according to the following procedure: A solution of methyl 5-methyl-1H-indole-6-carboxylate (100 mg, 0.529 mmol, 1.0 equiv), potassium iodide (8.8 mg, 0.053 mmol, 0.1 equiv), and sodium hydride (60% dispersion, 23.3 mg, 0.581 mmol, 1.1 equiv) in DMF (1.6 mL) was stirred at 0° C. for 1 h. Next, a solution of 1-(chloromethyl)-4-methoxybenzene (124 mg, 0.793 mmol, 1.5 equiv) in DMF (1 mL) was added, and the reaction mixture was heated to 65° C. for 2 h. The reaction was diluted in sat. $Na_2CO_{3(aq)}$ (50 mL) and extracted with EtOAc (3×25 mL). The combined organic extracts were washed with brine, dried over $MgSO_4$, filtered, and concentrated under reduced pressure. The resulting residue was purified by flash chromatography (hexanes/EtOAc) to yield methyl 1-(4-methoxybenzyl)-5-methyl-1H-indole-6-carboxylate (99.0 mg, 0.320 mmol, 61%). To a solution of methyl 1-(4-methoxybenzyl)-5-methyl-1H-indole-6-carboxylate (99.0 mg, 0.320 mmol, 1.0 equiv) and sodium hydroxide (64.0 mg, 1.60 mmol, 5.0 equiv) in 1:1 MeOH: THF (1.3 mL) was added 50% aqueous hydroxylamine (0.628 mL, 10.2 mmol, 32 equiv), and the resulting solution was stirred for 7 h. Upon reaction completion, 5 mL of water was added followed by removal of organic solvents under reduced pressure. Neutralization of the remaining aqueous solution with 1 M $HCl_{(aq)}$ resulted in the precipitation of product, which was filtered, washed with cold water, and dried under reduced pressure to yield BRD3811 (45.0 mg, 0.145 mmol, 45%) as a white powder in >95% purity (as determined by LCMS, ESI$^+$ MS: m/z: 311.7 [M+H]$^+$). $^1$H NMR (300 MHz, DMSO-d$_6$): δ 10.72 (br s, 1H), 8.97 (br s, 1H), 7.51 (d, J=2.8 Hz, 1H), 7.41 (s, 1H), 7.37 (s, 1H), 7.16 (d, J=8.4 Hz, 2H), 6.86 (d, J=8.4 Hz, 2H), 6.40 (d, J=2.8 Hz, 1H), 5.31 (s, 2H), 3.70 (s, 3H), 2.36 (s, 3H) ppm. For a $^1$H NMR spectrum, see FIG. 8*a*. For an HPLC trace demonstrating compound purity and detection of the appropriate mass, see FIG. 8*b*.

Caliper Assay.

The biochemical determination of HDAC IC$_{50}$s for compounds was performed as described previously (Zhang, Y.-L. et al., Fluorescent substrates for determining lysine modifying enzyme activity, 2013, Patent Application WO 2013067391). All HDACs were purchased from BPS Bioscience. The substrates Broad Substrate A and Broad Substrate B were synthesized in house, but can be purchased from PerkinElmer (Product number CLS960006 and CLS960007, respectively). All other reagents were purchased from Sigma. Caliper EZ reader II system was used to collect all data. Compounds were tested in duplicate in a 12-point dose curve with 3-fold serial dilution starting from 33.33 μM. Purified HDACs were incubated with 2 μM carboxyfluorescein (FAM)-labeled acetylated or trifluoroacetylated peptide substrate (Broad Substrate A and B, respectively) and test compound for 60 min at room temperature, in an HDAC assay buffer that contained 50 mM HEPES (pH 7.4), 100 mM KCl, 0.01% BSA and 0.001% Tween-20. Reactions were terminated by the addition of the known pan-HDAC inhibitor LBH-589 (panobinostat) with a final concentration of 1.5 μM. Substrate and product were separated electrophoretically and fluorescence intensity in the substrate and product peaks was determined and analyzed by Labchip EZ Reader. The percent inhibition was plotted against the compound concentration, and the IC$_{50}$ values were automatically fitted by Genedata Screener software using 4-parameter logistic dose response model. Inhibition of HDAC10 and 11 was not measured due to either low purity of the available recombinant HDAC enzyme preparations and/or lack of activity of the enzymes and low substrate conversion.

Molecular Docking.

The best pose of compound PCI-34051 in the HDAC8 binding site was determined using the zinc HDAC8 structure deposited in the PDB by Somozo et al. (accession code 1T64, Structure 2004, 1235-1334). Unresolved residues (33, 60, 69, 81, 85, 87-89, 221, 238, 377) were added using Prime, however, these residues would not be expected to be important interacting residues. Only one, Lys33, was near the ligand solvent-exposed end of the ligand after addition. Protonation of the structure and formation of sidechain-metal interactions was performed using the Protein Preparation Wizard followed by manual correction in the Schrodinger Drug Discovery Suite 2014-2. Histidines 142 and 143 were protonated at the delta nitrogen and histidine 180, which interacts with zinc at the delta position was protonated at the epsilon position. The binding ligand, Trichostatin A, was used as the center of the docking grid and the final cubic docking grid had the dimensions 10×10×10 Å$^3$ constructed using Schrodinger Glide 6.3 with default parameters. Glide XP was used to dock PCI-34051 and BRD3811 with options to enhance planarity of aromatic groups and to perform post-docking minization. The best docking pose for each was depicted in FIG. 1 using PyMol and coloring the surface within 5 Å by hydrophobicity using the color_h.py script detailed on the PyMol Wiki (http://www.pymolwiki.org/index.php/Color_h). PCI-34051 had a Glide XP score of −9.1 and the methyl analog, BRD3811, had a score of only −3.7 with significant decreases in the hydrogen bonding and Coloumbic score contributions. The docked geometry of BRD3811 does not permit binding with the metal center and the score should be considered exponentially worse than PCI-34051.

Cell Culture and Compound Treatment for SILAC Proteomics Experiments.

MCF7 cells were grown and expanded from the same frozen vial stock, followed by differentially labeling with non-radioactive stable isotopic amino acids by growing in light, medium, and heavy SILAC media (see below for recipe), respectively (Ong, S. E., et al. Mol. Cell Proteomics 5, 376-386 (2002)). MCF cells grown in SILAC medium were plated (2 million cells/plate, 10 mL per plate) into 10-cm tissue culture treated plates and incubated 24 h prior to treatment. For treatment, 10 µl of compounds (10 mM stocks in DMSO) or DMSO vehicle control were added to the plates, and the cells were incubated for 24 h. Next, the growth medium was aspirated, and the monolayers of cells were rinsed twice with cold PBS. Cells were detached using a cell scraper and collected with 1 ml of cold PBS. Cell pellets were harvested by centrifugation at 1,500 rpm for 1 min and flash frozen in liquid nitrogen. All pellets were stored in −80° C. freezer prior to lysis.

SILAC Media:
450 mL DMEM
50 mL FBS (Sigma, F-0392)
5 mL 100× Pen/Strep/Glutamine (Gibco 10378)
3.9 mL 45% Glucose solution (Sigma, G8769)
500 µL Methionine 0 (stock 30 g/L, final 30 mg/L)
500 µL Proline 0 (stock 20 g/L, final 20 mg/L)
500 µL Lysine 0 or Lysine 4 or Lysine 8 (stock 146 g/L, final 146 mg/L)
500 µL Arginine 0 or Arginine 6 or Arginine 10 (stock 84 g/L, final 84 mg/L)

Proteomics.

SILAC-labeled MCF-7 cells were lysed in ice-cold 8 M urea, 50 mM Tris-HCl (pH 7.5), 150 mM NaCl, 1 mM.

EDTA, 2 µg/ml aprotinin (Sigma-Aldrich), 10 µg/ml leupeptin (Roche Applied Science), 1 mM phenylmethylsulfonyl fluoride (PMSF), and 5 mM sodium butyrate (Sigma-Aldrich). Lysates were centrifuged at 20,000×g for 10 min at 4° C. to remove insoluble material. Protein concentrations were measured using a bicinchoninic acid (BCA) protein assay. For each replicate, 10 mg of protein per SILAC state was used for acetylation profiling. Proteins were reduced with 5 mM dithiothreitol for 45 min at RT. After reduction, proteins were alkylated using 10 mM iodoacetamide for 30 min at RT in the dark. Samples were diluted to 2 M urea and digested overnight with sequencing grade trypsin (Promega) using an enzyme to substrate ratio of 1:50 (w/w). TFA was used to quench digests. Peptide samples were desalted on tC 18 SepPak SPE cartridges (Waters) exactly as previously described[35]. Peptides were fractionated by basic pH reversed-phase (bRP) chromatography exactly as previously described[35]. Briefly, a Zorbax 300 Extend-C18 column (9.4×250 mm, 300 Å, 5 µm; Agilent) was used for the separation. Peptides were reconstituted in 5 mM ammonium formate (pH 10.0)/2% (vol/vol) acetonitrile (bRP Buffer A). Using the exact method parameters previously described, a total of 96 2 ml fractions were collected across the bRP separation. For acetylated (Kac) peptide analysis, each fraction was combined in a non-contiguous manner such that every eighth fraction was combined (final fraction 1=1, 9, 17, 25, 33, 41, 49, 57, 65; final fraction 2=2, 10, 18, 26, 34, 42, 50, 58, 66; . . . ) to create 8 final fractions. Pooled fractions were dried using vacuum centrifugation. An acetyl lysine antibody (Immunchem) was used for enrichment of Kac peptides from fractionated samples. Dried samples were reconstituted in 1.5 ml of 50 mM MOPS (pH 7.2), 10 mM sodium phosphate and 50 mM NaCl (II buffer). Peptides were incubated with 120 µg of anti-Kac antibody beads for 1 hr at 4° C. (with end-over-end rotation. Antibody beads were washed twice with 1.5 ml of ice-cold IP buffer followed by three washes with ice-cold PBS. Kac peptides were eluted from the antibody with 2×50 µl of 0.15% TFA. Enriched peptides were desalted using StageTips exactly as previously described. Samples were analyzed by nanoflow-UPLC-HCD-MS/MS using an Easy-nLC 1000 system (Proxeon) coupled online to a Q Exactive mass spectrometer (Thermo Fisher Scientific). Samples were reconstituted in 9 µl of 3% MeCN/0.1% formic acid and 4 µl was injected for analysis. Samples were injected at a flow rate of 500 nl/min onto a PicoFrit column (360 µm (OD)×75 µm (ID)), 10 µm ID tip, 50 cm length (New Objective) self-packed with 24 cm of ReproSil-Pur 120 Å, 1.9 µm C18-AQ beads and heated to 50° C. using a column heater (Pheonix S&T). The gradient and flow rate settings used were as previously described[35]. The Q Exactive was operated by acquiring an MS1 scan (R=70,000) followed by MS/MS scans on the 12 most abundant ions. For MS acquisition, ion targets of $3\times10^6$ and $5\times10^4$ ions were used for MS1 and MS2 scans, respectively. A maximum ion time of 20 ms and 120 ms was used for MS1 and MS2 scans, respectively. The HCD collision energy was set to 25. The dynamic exclusion time was set to 20 s and the peptide match and isotope exclusion functions were enabled. The MaxQuant software package (version 1.3.0.5) was used for identification and quantification of MS data. For searching, the enzyme specificity was set to trypsin, the maximum number of missed cleavages was set to 2, the precursor mass tolerance was set to 20 ppm for the first search, and the tolerance was set to 6 ppm for the main search. Carbamidomethylation of cysteines was searched as a fixed modification and oxidation of methionines, N-terminal acetylation of proteins, and acetylation of lysines were searched as variable modifications. The minimum peptide length was set to 6, and false discovery rate for peptide, protein, and site identification was set to 1%.

In Vitro Deacetylation Assay.

Peptides were purchased from Peptide 2.0 with a purity of >75% with an acetylated N-terminus and an amidated C-terminus and were resuspended in water. The concentrations of peptides containing an unmodified lysine were measured using the fluorescamine assay as previously described. All peptide concentrations were within two-fold of the calculated concentration based on weight. The CSRP2BP peptide contains no amine or aromatic amino acids; and therefore, the concentration was calculated based on the weight provided by Peptide 2.0. Recombinant human HDAC8 was either purchased or purified from E. coli as previously described[37] and all other HDAC homologues were purchased from BPS Biosciences. HDAC assays were performed using an enzyme-coupled system to measure acetate production as previously described[36]. The reactions were measured under standard HDAC reaction conditions (137 mM NaCl, 2.7 mM KCl, 25 mM HEPES, pH=7.8, 30° C.). Reactions measuring deacetylation of acetylated peptides (0-1600 µM) were initiated by addition of recombinant Zn(II)-HDAC8 (0.5-2.0 µM). The reactions were quenched by the addition of acid, and the acetate product, as reflected by an increase in the NADH fluorescence, was measured at 4 time points (up to 50 min). Recombinant HDAC isozymes 1-9 (0.4 µM), prepared by BPS Biosciences from baculovirus expression, were mixed with acetylated peptides (100

μM) and the formation of acetate product was measured as a function of time. The initial velocities ($v_0$) were calculated from a linear fit of the time-dependent increase in NADH fluorescence. The kinetic parameters were determined from fitting either a line or the Michaelis-Menten equation ($v_0$/[HDAC8]=$(k_{cat}[S])/(K_M+[S])$) to the dependence of the initial velocity on the peptide concentration. Inhibition of HDAC8-catalyzed deacetylation of ARID1A (100 μM, below $K_M$) by PCI-34051 was measured using the acetate assay in 2.7 mM KCl, 137 mM NaCl, 50 mM HEPES, pH=7.8, 0.001% BSA, 0.001% Tween 20. The value of $K_i$ was determined from a fit of $v_{obs}=v_0/(1+[I]/K_i)$ to the data.

Cell Culture and Compound Treatment for Gene Expression Experiments.

MCF7 cells (ATCC, #HTB-22) were cultured in DMEM medium (Gibco, #11995) containing 10% fetal bovine serum (Sigma, F4135) and 1× Pen Strep Glutamine (Gibco, #10378). Cells were plated into 384-well tissue culture treated plates (Corning, #3707) using a Multidrop Combi (Thermo, #5840300) at 2,000 cells per well. Cells were incubated for 24 hours at 37° C. in a humidified incubator containing 5% $CO_2$ before treatment.

Prior to treatment, 10 mM DMSO stock solutions of compounds were diluted to multiple doses in DMSO and arrayed into a 384-well plate (Abgene, #AB-1056). These 1,000× stock solutions were first diluted (100-fold) in culture medium, and then the diluted compounds were transferred to the cell culture plates using CyBi-well vario 384-well tips (another 10-fold dilution). Ultimately, all compounds were diluted 1,000-fold to their desired serial concentrations with a final DMSO concentration of 0.1%. Treated cells were incubated for 24 hours prior to lysis. Cells were lysed by partial removal of the culture media (15 μl remaining) followed by the addition of TCL lysis buffer (Qiagen, #1031576) using a liquid handling system. Cell lysate plates were sealed using a plate sealer, kept at room temperature for 30 minutes, and then frozen at −80° C. until L1000 gene expression profiling was performed. Detailed cell culture and treatment protocols for L1000 can be found at http://lincscloud.org.

Gene Expression Profiling.

In this study, we utilize L1000, a high-throughput, bead-based gene expression assay in which mRNA is extracted from cultured human cells treated with various chemical or genomic perturbagens (small molecules, gene knockdowns, or gene over-expression constructs) as previously described.[38] This mRNA is reverse-transcribed into first-strand cDNA. Gene specific probes containing barcodes and universal primer sites are annealed to the first strand cDNA. The probes are ligated to form a template for PCR. The template is PCR amplified with biotinylated-universal primers. The end products are biotinylated, fixed length, barcoded amplicons. The amplicons can then be mixed with Luminex beads that contain complementary barcodes to those encoded in each of the 1000 amplified landmark genes. These 1000 landmark genes were chosen as a reduced representation of the transcriptome and account for the majority of expression variation across many cellular contexts (Subramanian, et al., manuscript in preparation). These beads are then stained with fluorescent streptavidin-phycoerythrin (SAPE) and detected in 384-well plate format on a Luminex FlexMap flow cytometry-based scanner. The resulting readout is a measure of mean fluorescent intensity (MFI) for each landmark gene.

Connectivity Map Query Analysis.

The raw expression data are log 2-scaled, quantile normalized, and z-scored, such that a differential expression value is achieved for each gene in each well. In the standard L1000 protocol, each well corresponds to a different perturbagen and these differential expression values are collapsed across replicate wells to yield a differential expression signature for each perturbagen. The signatures of different perturbagens can then be compared to identify those that result in similar or dissimilar transcriptional responses as previously described.[39,40,41] In particular, to understand the mechanism of action of PCI-34051, we sought to identify connections that persisted across multiple distinct tissue types reasoning such connections are most robust. To assess this, we did a meta-analysis of the CMap query results (i.e., lists of perturbations ordered by similarity to an input gene expression signature). The input signature consisted of the 100 most differentially expressed genes (50 up and 50 down) upon treatment with PCI-34051. We performed the same analysis with BRD3811 as well.

When queried across the L1000 database at lincscloud.org, this produced a ranked list of 476251 connections corresponding to 51385 unique perturbagens. To summarize, the query result is first grouped by cell line and perturbagen type (small molecule, gene knockdown, or overexpression). The connectivity scores are then normalized by dividing by the signed mean score of each group. The scores are converted to percentile ranks within each group. The perturbagens are then ranked according to the direction of connectivity. Positive connections are ranked highest, and negative connections ranked lowest. For each unique perturbagen, we considered the average percentile rank in the four cell lines for which the connection to the query was strongest.

Western Blotting.

MCF7 cells were treated with compounds for 48 h, at which time, lysates were collected using RIPA buffer with added protease (Roche) and phosphatase (Roche) inhibitors. Electrophoresis was performed using NuPage 4-12% Bis-Tris gels (Invitrogen). Proteins were transferred to a nitrocellulose membrane and probed using antibodies for p21 (Cell Signaling) and GAPDH (Cell Signalling). Chemiluminescence was induced by subsequent incubation with HRP-linked secondary antibodies (GE Healthcare UK Ltd.) and treatment of the membrane with the appropriate ECL solutions (Thermo Scientific). Visualization was accomplished using a ChemiDoc MP System (Bio-Rad), and the raw data files were converted to jpegs using ImageJ (NIH).

Conjugates of Formula I can be synthesized using methods similar to the ones described in (WO2013067391; Fluorescent substrates for determining lysine modifying enzyme activity).

While this invention has been particularly shown and described with references to preferred embodiments thereof, it will be understood by those skilled in the art that various changes in form and details may be made therein without departing from the scope of the invention encompassed by the appended claims.

APPENDIX A

Supplementary Table 4

| Probe.ID | raw_p_values | BH_adjusted_p_values | symbol | direction | fold_change_at_10_uM |
|---|---|---|---|---|---|
| 203665_at | <1.06E−16 | <1.06E−16 | HMOX1 | u | 18.123965 |
| 201266_at | <1.06E−16 | <1.06E−16 | TXNRD1 | u | 3.555996771 |
| 202284_s_at | <1.06E−16 | <1.06E−16 | CDKN1A | u | 2.508266502 |
| 202220_at | <1.06E−16 | <1.06E−16 | KIAA0907 | u | 2.461947909 |
| 203192_at | <1.06E−16 | <1.06E−16 | ABCB6 | u | 2.438824614 |
| 222125_s_at | <1.06E−16 | <1.06E−16 | P4HTM | u | 2.379433364 |
| 202887_s_at | <1.06E−16 | <1.06E−16 | DDIT4 | u | 2.33983487 |
| 203911_at | <1.06E−16 | <1.06E−16 | RAP1GAP | u | 2.278022872 |
| 201536_at | <1.06E−16 | <1.06E−16 | DUSP3 | u | 2.207711204 |
| 204014_at | <1.06E−16 | <1.06E−16 | DUSP4 | u | 2.052066735 |
| 202100_at | <1.06E−16 | <1.06E−16 | RALB | u | 1.945537042 |
| 216836_s_at | <1.06E−16 | <1.06E−16 | ERBB2 | u | 1.887840991 |
| 200678_x_at | <1.06E−16 | <1.06E−16 | GRN | u | 1.867966887 |
| 210788_s_at | <1.06E−16 | <1.06E−16 | DHR57 | u | 1.835587969 |
| 208626_s_at | <1.06E−16 | <1.06E−16 | VAT1 | u | 1.773712625 |
| 203456_at | <1.06E−16 | <1.06E−16 | PRAF2 | u | 1.761208568 |
| 202708_at | <1.06E−16 | <1.06E−16 | HIST2H2BE | u | 1.757652569 |
| 209112_at | <1.06E−16 | <1.06E−16 | CDKN1B | u | 1.719137254 |
| 205451_at | <1.06E−16 | <1.06E−16 | FOXD4 | u | 1.718793893 |
| 201471_s_at | <1.06E−16 | <1.06E−16 | SQSTM1 | u | 1.657958029 |
| 202087_s_at | <1.06E−16 | <1.06E−16 | CTSL | u | 1.650959558 |
| 201847_at | 0.002 | 0.027942857 | LIPA | u | 1.648608948 |
| 218845_at | <1.06E−16 | <1.06E−16 | DUSP22 | u | 1.616205915 |
| 202996_at | <1.06E−16 | <1.06E−16 |  | u | 1.606905248 |
| 205633_s_at | <1.06E−16 | <1.06E−16 | ALAS1 | u | 1.588671547 |
| 203409_at | <1.06E−16 | <1.06E−16 | DDB2 | u | 1.584257472 |
| 201397_at | <1.06E−16 | <1.06E−16 | PGHDH | u | 1.578569416 |
| 209179_s_at | <1.06E−16 | <1.06E−16 | MBOAT7 | u | 1.578054989 |
| 212300_at | 0.002 | 0.027942857 | TXLNA | u | 1.570797342 |
| 201432_at | <1.06E−16 | <1.06E−16 | CAT | u | 1.54702062 |
| 202282_at | <1.06E−16 | <1.06E−16 | HSD17810 | u | 1.529086435 |
| 200789_at | 0.002 | 0.027942857 |  | u | 1.512190474 |
| 202630_at | <1.06E−16 | <1.06E−16 | APPBP2 | u | 1.492849883 |
| 202603_at | 0.002 | 0.027942857 | GATA3 | u | 1.427455472 |
| 201746_at | <1.06E−16 | <1.06E−16 | TP53 | u | 1.427299676 |
| 202224_at | <1.06E−16 | <1.06E−16 | CRK | u | 1.424000829 |
| 201462_at | 0.002 | 0.027942857 | SCRN1 | u | 1.418274225 |
| 210416_s_at | <1.06E−16 | <1.06E−16 | CHEK2 | u | 1.417805826 |
| 202812_at | 0.002 | 0.027942857 | GAA | u | 1.414477658 |
| 201719_s_at | 0.002 | 0.027942857 | EPB41L2 | u | 1.387708114 |
| 201174_s_at | 0.002 | 0.027942857 | TERF2IP | u | 1.386305414 |
| 207805_s_at | <1.06E−16 | <1.06E−16 | PSMD9 | u | 1.344522105 |
| 200757_s_at | <1.06E−16 | <1.06E−16 | CALU | u | 1.307060467 |
| 202716_at | 0.002 | 0.027942857 | PTPN1 | u | 1.301494688 |
| 202117_at | 0.002 | 0.027942857 | ARGHGAP1 | u | 1.295329531 |
| 203167_at | 0.002 | 0.027942857 | TIMP2 | u | 1.284217187 |
| 201855_s_at | 0.002 | 0.027942857 | ATMIN | u | 1.276206282 |
| 214710_s_at | <1.06E−16 | <1.06E−16 | CCNB1 | d | 0.834853541 |
| 202246_s_at | <1.06E−16 | <1.06E−16 | CDK4 | d | 0.774183865 |
| 202900_s_at | <1.06E−16 | <1.06E−16 | NUP88 | d | 0.753700075 |
| 203228_at | <1.06E−16 | <1.06E−16 | PAFAH1B3 | d | 0.736181359 |
| 201186_at | <1.06E−16 | <1.06E−16 | LRPAP1 | d | 0.703362563 |
| 202788_at | <1.06E−16 | <1.06E−16 | MAPKAPK3 | d | 0.702615586 |
| 209095_at | <1.06E−16 | <1.06E−16 | DLD | d | 0.689526741 |
| 202427_s_at | <1.06E−16 | <1.06E−16 | MPC2 | d | 0.667902895 |
| 201626_at | <1.06E−16 | <1.06E−16 | INSIG1 | d | 0.662362709 |
| 204549_at | 0.002 | 0.027942857 | IKBKE | d | 0.654935648 |

APPENDIX 2

Supplementary Table 5

| Probe.ID | raw_p_values | BH_adjusted_p_values | symbol | direction | fold_change_at_10_uM |
|---|---|---|---|---|---|
| 203665_at | p < 1.06E−16 | <1.06E−16 | HMOX1 | u | 2.066792123 |
| 202284_s_at | p < 1.06E−16 | <1.06E−16 | CDKN1A | u | 1.956249877 |
| 206562_s_at | p < 1.06E−16 | <1.06E−16 | CSNK1A1 | u | 1.62266424 |
| 216836_s_at | p < 1.06E−16 | <1.06E−16 | ERBB2 | u | 1.61429508 |
| 201536_at | p < 1.06E−16 | <1.06E−16 | DUSP3 | u | 1.585570022 |
| 208626_s_at | p < 1.06E−16 | <1.06E−16 | VAT1 | u | 1.388896575 |

APPENDIX 2-continued

Supplementary Table 5

| Probe.ID | raw_p_values | BH_adjusted_p_values | symbol | direction | fold_change_at_10_uM |
|---|---|---|---|---|---|
| 201266_at | p < 1.06E−16 | <1.06E−16 | TXNRD1 | u | 1.298027201 |
| 205498_at | p < 1.06E−16 | <1.06E−16 | GHR | d | 0.72866779 |
| 202458_at | p < 1.06E−16 | <1.06E−16 | PRSS23 | d | 0.650737536 |
| 208025_s_at | p < 1.06E−16 | <1.06E−16 | HMGA2 | d | 0.607326787 |
| 212833_at | p < 1.06E−16 | <1.06E−16 | SLC25A46 | d | 0.563523464 |

---

What is claimed is:

1. A compound of Formula II:

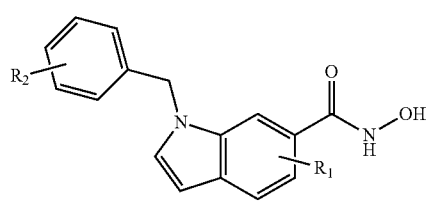

II or a pharmaceutically acceptable salt or ester thereof; wherein $R_1$ is selected from halogen, $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkynyl and substituted $C_1$-$C_6$ alkynyl; and, $R_2$ is selected from —O—$C_1$-$C_6$ alkyl, substituted —O—$C_1$-$C_6$ alkyl, —S$C_1$-$C_6$ alkyl and substituted —S$C_1$-$C_6$ alkyl.

2. The compound of claim 1 having the formula:

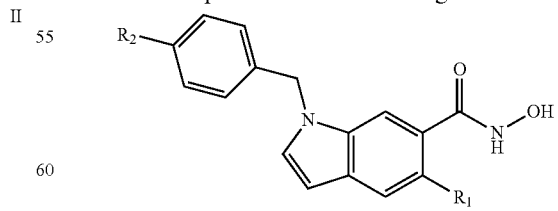

or a pharmaceutically acceptable salt or ester thereof; wherein $R_1$ is selected from the group consisting of F, Cl, I, methyl, ethyl, propyl, isopropyl, n-butyl, t-butyl and $CF_3$; and $R_2$ is $OCH_3$ or —$OCH_2CH_3$.

3. The compound of claim 1 having the formula:
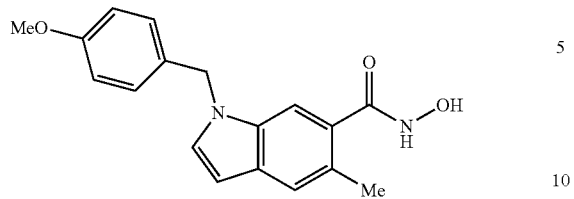
or a pharmaceutically acceptable salt thereof.
\* \* \* \* \*

SEQUENCE LISTING

<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 1

Lys Leu Gly Gly Lys Gln Arg Ala Ala
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 2

Thr Glu Ile Gly Lys Thr Leu Ala Glu Lys
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 3

Leu Gly Asp Gly Lys Met Lys Ser
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (6)..(6)
<223> OTHER INFORMATION: ACETYLATION

<400> SEQUENCE: 4

Lys Arg Ile Leu His Lys Leu Leu Gln Asn
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 5

Lys Leu Ser Gly Lys Glu Ile Asn Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 6

Lys Leu Ile Ser Lys Phe Asp Lys Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 7

Ser Thr Pro Val Lys Phe Ile Ser Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION
```

```
<400> SEQUENCE: 8

Ser Lys Ile Gln Lys Gln Leu Asp Gln
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(7)
<223> OTHER INFORMATION: ACETYLATION

<400> SEQUENCE: 9

Arg Val Ile Gly Ala Lys Lys Asp Gln Tyr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 10

Lys Leu Gly Gly Lys Gln Arg Ala Ala
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 11

Thr Glu Ile Gly Lys Thr Leu Ala Glu Lys
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 12

Leu Gly Asp Gly Lys Met Lys Ser
1               5

<210> SEQ ID NO 13
<211> LENGTH: 10
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: ACETYLATION

<400> SEQUENCE: 13

Lys Arg Ile Leu His Lys Leu Leu Gln Asn
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 14

Lys Leu Ser Gly Lys Glu Ile Asn Gly
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 15

Lys Leu Ile Ser Lys Phe Asp Lys Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 16

Ser Thr Pro Val Lys Phe Ile Ser Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 17

Ser Lys Ile Gln Lys Gln Leu Asp Gln
1               5
```

```
<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(7)
<223> OTHER INFORMATION: ACETYLATION

<400> SEQUENCE: 18

Arg Val Ile Gly Ala Lys Lys Asp Gln Tyr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: ACETYLATION

<400> SEQUENCE: 19

Lys Phe Asp Lys Leu
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: ACETYLATION

<400> SEQUENCE: 20

Ser Lys Phe Asp Lys Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: ACETYLATION

<400> SEQUENCE: 21

Ile Ser Lys Phe Asp Lys Leu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
```

<223> OTHER INFORMATION: ACETYLATION

<400> SEQUENCE: 22

Leu Ile Ser Lys Phe Asp Lys Leu
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 23

Lys Leu Ile Ser Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 24

Lys Leu Ile Ser Lys Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 25

Lys Leu Ile Ser Lys Phe Asp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: ACETYLATION

<400> SEQUENCE: 26

Lys Leu Ile Ser Lys Phe Asp Lys
1               5

<210> SEQ ID NO 27
<211> LENGTH: 5
<212> TYPE: PRT

<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: COCF3

<400> SEQUENCE: 27

Lys Phe Asp Lys Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: COCF3

<400> SEQUENCE: 28

Ser Lys Phe Asp Lys Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: COCF3

<400> SEQUENCE: 29

Ile Ser Lys Phe Asp Lys Leu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: COCF3

<400> SEQUENCE: 30

Leu Ile Ser Lys Phe Asp Lys Leu
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: COCF3

```
<400> SEQUENCE: 31

Lys Leu Ile Ser Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: COCF3

<400> SEQUENCE: 32

Lys Leu Ile Ser Lys Phe
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: COCF3

<400> SEQUENCE: 33

Lys Leu Ile Ser Lys Phe Asp
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: COCF3

<400> SEQUENCE: 34

Lys Leu Ile Ser Lys Phe Asp Lys
1               5
```